(12) United States Patent
Dewaele et al.

(10) Patent No.: US 8,398,587 B2
(45) Date of Patent: Mar. 19, 2013

(54) STEERABLE TUBE

(75) Inventors: Frank Dewaele, De Pinte (BE); Cyriel Mabilde, Oudenaarde (BE); Bart Blanckaert, Eeklo (BE)

(73) Assignee: Steerable Instruments B.V.B.A., Eeklo (BE)

( * ) Notice: Subject to any disclaimer, the term of this patent is extended or adjusted under 35 U.S.C. 154(b) by 175 days.

(21) Appl. No.: 12/866,003

(22) PCT Filed: Feb. 5, 2009

(86) PCT No.: PCT/EP2009/051294

§ 371 (c)(1),
(2), (4) Date: Aug. 3, 2010

(87) PCT Pub. No.: WO2009/098244

PCT Pub. Date: Aug. 13, 2009

(65) Prior Publication Data

US 2011/0004157 A1  Jan. 6, 2011

(30) Foreign Application Priority Data

Feb. 5, 2008 (EP) .................................. 08151060

(51) Int. Cl.
*A61M 31/00* (2006.01)
(52) U.S. Cl. ...................... 604/95.04; 604/525; 604/528; 600/101; 600/125
(58) Field of Classification Search ............... 604/95.01, 604/95.04, 523–526, 528; 600/101, 121, 600/125
See application file for complete search history.

(56) References Cited

U.S. PATENT DOCUMENTS

| 5,284,130 A | 2/1994 | Ratliff |
| 5,599,151 A | 2/1997 | Daum et al. |

(Continued)

FOREIGN PATENT DOCUMENTS

| EP | 1 321 106 | 6/2003 |
| EP | 1 611 864 | 1/2006 |

(Continued)

OTHER PUBLICATIONS

International Search Report dated Aug. 19, 2009 issued to international application No. PCT/EP2008/051294.

*Primary Examiner* — Nicholas Lucchesi
*Assistant Examiner* — Melissa A Snyder
(74) *Attorney, Agent, or Firm* — Knobbe Martens Olson & Bear LLP

(57) ABSTRACT

A steerable tube (100), comprising a hollow elongate tubular member (1) having a proximal end (2), distal end (3), a wall surface disposed between said proximal (2) and distal end (4), a bend-resistive zone (6) flanked by a proximal bendable zone (4) that forms a controller and a distal bendable zone (5) that forms an effector that moves responsive to movements of the controller, whereby the wall of the tubular member (1) in the bend-resistive zone (6) comprises a structure that is a plurality of longitudinal slits (7), forming a plurality of longitudinal strips (8, 8'), the wall of the tubular member (1) in the proximal bendable zone (4) and the distal bendable zone (5) comprises a structure that is a plurality of longitudinal wires (9, 9', 10, 10'), at least one strip (8) is in connection with a wire (9) in the proximal bendable zone (4) and a wire (10) in the distal bendable zone (5), such that translation by said wire (9) in the controller is transmitted via the strip (8) to said wire (10) in the effector, a proximal annular region (11) of the tubular member (1), proximal to the proximal bendable zone (4) to which the proximal wires (9) are anchored, a distal annular region (12) of the tubular member (1) distal to the distal bendable zone (5) to which the distal wires (10) are anchored.

25 Claims, 19 Drawing Sheets

U.S. PATENT DOCUMENTS

| | | |
|---|---|---|
| 5,776,126 A | 7/1998 | Wilk et al. |
| 7,682,307 B2 * | 3/2010 | Danitz et al. .................. 600/141 |
| 2005/0273085 A1 | 12/2005 | Hinman et al. |
| 2006/0178556 A1 | 8/2006 | Hasser et al. |
| 2006/0259018 A1 | 11/2006 | Shilkrut |
| 2007/0005090 A1 | 1/2007 | Whitmore, III et al. |
| 2007/0277815 A1 | 12/2007 | Ravikumar et al. |

FOREIGN PATENT DOCUMENTS

| | | |
|---|---|---|
| WO | WO 03/037416 | 5/2003 |
| WO | WO 2004/026105 | 4/2004 |
| WO | WO 2004/086957 | 10/2004 |
| WO | WO 2008/140890 | 11/2008 |
| WO | WO 2009/112060 | 9/2009 |

* cited by examiner

PRIOR ART

O.D. 2.3mm
I.D. 0.76

O.D. 2.3mm
I.D. 0.76

A

B

O.D. 2.3mm
I.D. 1.6

STEERABLE TUBE

FIELD OF THE INVENTION

The invention relates to a steerable tube having enhanced control and simplified construction, which can be used in high-precision or medical applications.

BACKGROUND OF THE INVENTION

The invention relates to an instrument for high-precision mechanical applications or for medical applications (e.g. surgery, endovascular procedures, or for use as an endoscope) of a minimally invasive nature, comprising a hollow tubular member (1) having a proximal bendable zone (4) that forms a controller head, a distal bendable zone (5) that forms an effector—a steerable tip—and flexes responsive to movements of the controller, and, a bend-resistive zone (6) between the aforementioned zones (4, 5), that transmits movements of the controller to the effector. The member is preferably formed from one or more substantially solid walled tubes. The high-precision instrument find applications where exquisite, remote movements in confined spaces are needed, such as in medical applications, and in the inspection and repair of encased devices such as engines, pipelines, valves and other mechanical systems.

The notion an instrument having a steerable tip is known in the art. For instance, WO 03/037416 describes a mechanism that deflects portions of a flexible body such as a catheter in more than one direction in a single plane, as well as in more than one plane by use of a pullwire. In order to control the deflection of the distal end, many designs incorporate one or more steering cables. Mostly these cables are fed through guide-sleeves located in the wall of the tube or in its lumen. These guide-sleeves that hold the steering cables in place are bulky and add to the cross-section of the wall.

For example, US-A-2006/0178556 (See FIGS. 1A and 1C), describes a steerable device having a ring of longitudinally extending cables 101 connecting to the head, which cables are fixedly secured in the radial direction. A disadvantage of this instrument is, however, that the cables are fed through guide-sleeves 102 provided in the longitudinal direction of the cables, which increase the diameter of the instrument.

A system to omit these sleeves has been described in WO 02/13682 (see FIGS. 1B and 1D) which discloses a steerable device also of a ring of cables 103 comprising longitudinally extending cables connected to the head, which cables are fixedly secured in the radial direction. Instead of the cables being fed through guide-sleeves as in US-A-2006/0178556, they are disposed side by side so filling the space where the guide sleeves would otherwise be. A disadvantage of this system is the high construction cost for devices where lumen diameters need to be maximised for a given outer diameter—i.e. the walls made thin which is a requirement for most applications. A rapid increase in the number of steering wires is seen when increasing the internal diameter while maintaining a thin wall, for example, 25 steering cables of 0.2 mm for a lumen of 1 mm diameter. Furthermore, the alignment and correct pre-tensioning of a large number of narrow diameter wires represents an enormous technical challenge. Further it is anticipated that the wires of narrowed diameter may slip circumferentially within the sleeve, and tangle or wear.

It remains challenging to make an adequate affixation with the head and tip. Standard affixation techniques include soldering, clamping, crimping, use of small bolts, glue, knotting, cable U-turns through rigid termination disk or laser-welding. Mostly these affixation techniques result in bulky joints and some of them even weaken the wires.

Additionally, a compression spring is used in the art to pre-stress the tip, however, this reduces its torsion and bending stability, meaning the tip can readily be deflected from a bent position by the application of an external force to the tip. Moreover, axial compression, for example, by pulling the tool control wire during operation of the surgical tool can induce straightening of the tip—a phenomenon known as crosstalk which is to be avoided.

One particular application of a steerable tube is in the field of neurosurgery. Neurosurgical endoscopic intraventricular procedures are typically performed with a neurosurgical instrument known as the Caemaert endoscope. It is a long rigid shaft with an external diameter of ~6 mm and four lumens. One lumen is for an optic element, one for a working channel, and two for rinsing fluid. The endoscope is introduced through a burr hole in the skull; the shaft intrudes the brain tissue at a non-eloquent area before entering the fluid filled ventricles. To reach the most central ventricle—known as the third ventricle—passage through an important ring-like structure, the foramen of Monroe, is necessary. Damage to this structure causes amnesia. Access to the third ventricle allows several surgical procedures to be performed such as perforating membranes or removing tumors. The latter is the most challenging procedure, requiring the sequential use of coagulation, grasping and aspiration. Using present technology, it is not possible to have more than one steerable tube inside the endoscopic shaft, especially when one of the tubes is a steerable aspiration catheter which also requires a large lumen compatible with removal of particles of tissue.

The present invention, therefore, address the problems of the art by providing a steerable tube having a large diameter lumen while minimizing the outer diameter, which is reliable and cost-effective to manufacture.

SUMMARY OF THE INVENTION

One embodiment of the invention is a steerable tube (100), comprising a hollow elongate tubular member (1) having a proximal end (2), distal end (3), a wall surface disposed between said proximal (2) and distal end (4), the wall having a substantially uniform thickness, a bend-resistive zone (6) flanked by a proximal bendable zone (4) that forms a controller and a distal bendable zone (5) that forms an effector, whereby

- the wall of the tubular member (1) in the bend-resistive zone (6) comprises a structure that is a plurality of longitudinal slits (7), forming a plurality of longitudinal strips (8, 8'),
- the wall of the tubular member (1) in the proximal bendable zone (4) and the distal bendable zone (5) comprises a structure that is a plurality of longitudinal wires (9, 9', 10, 10'),
- at least one strip (8) is in connection with a wire (9) in the proximal bendable zone (4) and a wire (10) in the distal bendable zone (5), such that translation by said wire (9) in the controller is transmitted via the strip (8) to said wire (10) in the effector,
- a proximal annular region (11) of the tubular member (1), proximal to the proximal bendable zone (4) is circumferentially intact,
- a distal annular region (12) of the tubular member (11) distal to the distal bendable zone (5) is circumferentially intact.

Another embodiment of the invention is a steerable tube (100), comprising a hollow elongate tubular member (1) having a proximal end (2), distal end (3), a wall surface disposed between said proximal (2) and distal end (4), a bend-resistive zone (6) flanked by a proximal bendable zone (4) that forms a controller and a distal bendable zone (5) that forms an effector, whereby the wall of the tubular member (1) in the bend-resistive zone (6) comprises a structure that is a plurality of longitudinal slits (7), forming a plurality of longitudinal strips (8, 8'), the wall of the tubular member (1) in the proximal bendable zone (4) and the distal bendable zone (5) comprises a structure that is a plurality of longitudinal wires (9, 9', 10, 10'), at least one strip (8) is in connection with a wire (9) in the proximal bendable zone (4) and a wire (10) in the distal bendable zone (5), such that translation by said wire (9) in the controller is transmitted via the strip (8) to said wire (10) in the effector, a proximal annular region (11) of the tubular member (1), proximal to the proximal bendable zone (4) to which the proximal wires (9) are anchored, a distal annular region (12) of the tubular member (1) distal to the distal bendable zone (5) to which the distal wires (10) are anchored.

Another embodiment of the invention is a steerable tube (100) as described above, wherein one or more of the longitudinal strips (8, 8') is aligned or inclined to a longitudinal (A-A') axis of the hollow elongate tubular member (1).

Another embodiment of the invention is a steerable tube (100) as described above, wherein one or more of the longitudinal strips (8, 8') is at least partly linear.

Another embodiment of the invention is a steerable tube (100) as described above, wherein one or more of the longitudinal strips (8, 8') is provided with interconnections, non-radial slits or spiral cuts to hold the strips together.

Another embodiment of the invention is a steerable tube (100) as described above, wherein the plurality of longitudinal wires (9, 9', 10, 10') are separated by longitudinal apertures (13, 13', 14, 14') in the proximal bendable zone (4) and/or a distal bendable zone (5).

Another embodiment of the invention is a steerable tube (100) as described above, wherein a wire (9, 9', 10, 10') in a bendable zone (4, 5) is more narrow than a strip (8) in the bend-resistive zone (6).

Another embodiment of the invention is a steerable tube (100) as described above, wherein the circumferential width of a wire (9, 9', 10, 10') in the narrowest part, is between 50%, and 90% less than the circumferential width of a strip (8) in the narrowest part.

Another embodiment of the invention is a steerable tube (100) as described above, wherein the circumferential width of a wire (9, 9', 10, 10') in the narrowest part, is between 0%, and 90% less than the circumferential width of a strip (8) in the narrowest part.

Another embodiment of the invention is a steerable tube (100) as described above, wherein one or more of the wires (9, 9', 10, 10') is aligned or inclined to a longitudinal (A-A') axis of the hollow elongate tubular member (1).

Another embodiment of the invention is a steerable tube (100) as described above, wherein one or more of the wires (9, 9', 10, 10') is at least partly linear.

Another embodiment of the invention is a steerable tube (100) as described above, wherein the proximal bendable zone (4) and/or distal bendable zone (5) is substantially formed from a material different to that of the bend-resistive zone (6).

Another embodiment of the invention is a steerable tube (100) as described above, further comprising an outer sheath (20), at least partly covering the outside surface of the hollow elongate tubular member (1) while permitting translational movements of the strips (8, 8') and wires (9, 9', 10, 10') within.

Another embodiment of the invention is a steerable tube (100) as described above, wherein the outer sheath (20), is flexible in the region covering at least the bendable zones (4, 5).

Another embodiment of the invention is a steerable tube (100) as described above, wherein the outer sheath (20), is less flexible in the region covering the bend-resistive zone (6) compared with in the region covering at least the bendable zones (4, 5).

Another embodiment of the invention is a steerable tube (100) as described above, further comprising an inner lining (50) that at least partly lines the lumen (15) of the hollow elongate tubular member (1) while permitting translational movements of the strips (8, 8') and wires (9, 9', 10, 10') outside.

Another embodiment of the invention is a steerable tube (100) as described above, whereby one or more of the apertures (13, 13', 14, 14') between the wires (9, 9', 10, 10') is provided with a spacer (16).

Another embodiment of the invention is a steerable tube (100) as described above, further comprising a handgripper (70) at the proximal end (2), configured to control a set of forceps (80) at the distal end (3).

Another embodiment of the invention is a steerable tube (100) as described above, further comprising an endoscopic camera or lens at the distal end (3).

Another embodiment of the invention is a steerable tube (100) as described above, further comprising a cutting tool (scissors, knife, drill, mill, grinder, knibbler) at the distal end (3).

Another embodiment of the invention is a steerable tube (100) as described above, further comprising a sensor (temperature, moisture, light, gas, radioactivity) at the distal end (3).

Another embodiment of the invention is a steerable tube (100) as described above, further comprising electrodes (stimulation, recording, coagulation) at the distal end (3).

Another embodiment of the invention is a steerable tube (100) as described above, whereby the zones are formed from a substantially solid tube wall of the hollow tubular member during manufacture, and the bendable zones are formed by removing material from said substantially solid tube wall.

Another embodiment of the invention is a steerable tube (100) as described above, whereby a wire (9) in the proximal bendable zone (4) and/or a wire (10) in the distal bendable zone (5) is disposed with one or more cuts configured to increase flexibility of said wire Another embodiment of the invention is a steerable tube (100) as described above, whereby the proximal annular region (11) and/or distal annular region (12) are formed from one or more circumferentially interlocking elements.

Another embodiment of the invention is a steerable tube (100) as described above, whereby a wire (9) in the proximal bendable zone (4) and/or a wire (10) in the distal bendable zone (5) is connected to a strip by welding, gluing, soldering or by interlocking.

Another embodiment of the invention is a steerable tube (100) as described above, whereby the thickness of a wire (9) in the proximal bendable zone (4) in its thinnest region and/or a wire (10) in the distal bendable zone (5) is less than that of a connecting strip (8) in its thinnest region.

Another embodiment of the invention is a steerable tube (100) as described above, whereby a wire (9) in the proximal bendable zone (4) and/or a wire (10) in the distal bendable zone (5) is made from a more flexible material than use in a connecting strip (8).

Another embodiment of the invention is a steerable tube (100) as described above, wherein the elongate tubular member (1) comprises a side port (40) formed from an aperture between two adjacent strips (8, 8').

Another embodiment of the invention is a steerable tube (100) as described above, wherein the elongate tubular member (1) incorporates a limit stop mechanism (41) that limits the extent of relative slidable movement between two strips (8, 8').

Another embodiment of the invention is a steerable tube (100) as described above, whereby elongate tubular member (1), and one of the outer sheath (20), or inner lining (50) are coaxially rotatable elements, further comprises a rotation limiting mechanism (44, 44') formed from a radial protrusion (45a, 45'a) present in any one coaxially rotatable element, in longitudinal slidable connection with a reciprocating slot (45b, 45'b) in another coaxially rotatable element of the steerable tube (100) configured to reduce or prevent revolute movement by the elongate tubular member (1) relative to the outer sheath (20) or inner lining (50).

Another embodiment of the invention is a steerable tube (100) as described above, further comprising an electromechanical actuator configured to controllably move the proximal bendable zone (4) within its range of movement, and optionally to rotate the steerable tube (100) around its longitudinal (A-A') axis.

Another embodiment of the invention is a steerable tube (100) as described above, further a braking mechanism, configured, to prevent slidable movements by the strips (8, 8') relative to the outer sheath (20) or inner lining (50).

Another embodiment of the invention is a steering guide (119—FIG. 17) comprising an elongated longitudinal member (122) having a proximal (126) and distal (128) end, the proximal end (126) disposed with a brace (123) for attachment to a part of a bodily arm, and the distal end (128) disposed with an endoport (160) configured for attachment to a medical instrument (120), said steering guide configured to place a proximal end (126) of the instrument in the vicinity of the hand (138) of said arm, and for pivotal movement of the instrument (120) actuated by movement said part of the arm.

Another embodiment of the invention is a lockable articulated arm (170—FIG. 18) comprising a plurality of tandemly arranged, rigid links (172, 174, 176, 178) connected by lockable joints (180, 182, 184) having at one end a base link (172) configured for rigid attachment to an operating table (171), and at the other end, an effector link (178) connected to a lockable ball and socket joint (152), the ball and socket joint configured for coupling to an endoport device (160), through which a medical instrument (120) is disposed, which lockable ball joint (152) is further configured to pivot the endoport device (160) relative to the effector link (178).

Another embodiment of the invention is a rotation limiting mechanism for a steerable tube comprising a plurality of cables arranged in a cylinder, circumferentially flanked by an inner and outer tubular support whereby the cylindrically arranged cables, and one of the inner and outer tubular supports are coaxially rotatable elements, which rotation limiting mechanism is formed from a radial protrusion present in any one coaxially rotatable element, in longitudinal slidable connection with a reciprocating slot in another coaxially rotatable element of the steerable tube configured to reduce or prevent coaxially rotation by the cylindrically arranged cables relative to the inner or outer tubular support.

BRIEF DESCRIPTION OF THE FIGURES

In FIG. 6A, alternate wires are bent in an undulating form, in FIG. 6B, the wires are disposed with teeth, in FIG. 6C the wires is disposed with hollow rings.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and "an" are used herein to refer to one or to more than one, i.e. to at least one of the grammatical object of the article. By way of example, "a linkage" means one linkage or more than one linkage.

The recitation of numerical ranges by endpoints includes all integer numbers and, where appropriate, fractions subsumed within that range (e.g. 1 to 5 can include 1, 2, 3, 4 when referring to, for example, a number of object, and can also include 1.5, 2, 2.75 and 3.80, when referring to, for example, measurements). The recitation of end points also includes the end point values themselves (e.g. from 1.0 to 5.0 includes both 1.0 and 5.0)

The terms "distal" and "proximal" are used through the specification, and are terms generally understood in the field to mean towards (proximal) or away (distal) from the surgeon's side of the apparatus. Thus, "proximal" means towards the surgeon's side and, therefore, away from the patient's side. Conversely, "distal" means towards the patient's side and, therefore, away from the surgeon's side.

Reference is made in the description below to the drawings which exemplify particular embodiments of the invention; they are not at all intended to be limiting. It will be understood that the skilled person may adapt the device and substitute components and features according to the common practices of the skilled artisan.

Figure 3:
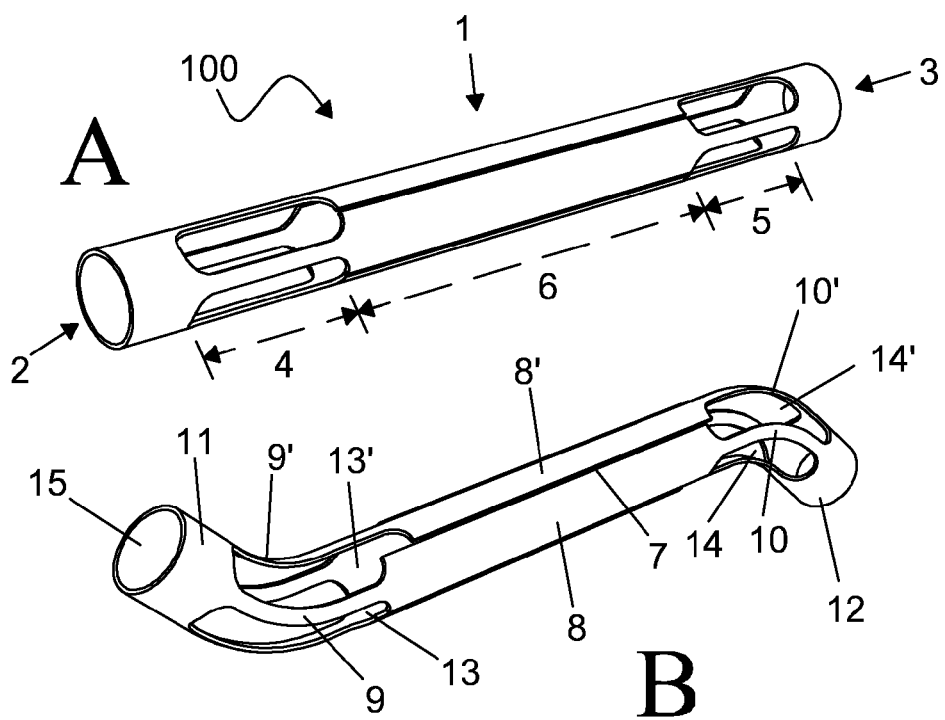
FIG. 3A depicts a perspective view of a steerable tube of the present invention in a non-bent state.
FIG. 3B depicts a perspective view of a steerable tube of the present invention whereby the proximal and distal bendable zones are flexed.

The present invention relates to a steerable tube with thin-walls and having ends that can move in omni-directional manner and are mechanically coupled. With reference to FIGS. 3A and B an embodiment of the present invention concerns steerable tube 100, comprising a hollow elongate tubular member 1 having a proximal end 2, a distal end 3, a wall surface disposed between said proximal 2 and distal end 3, a bend-resistive zone 6 flanked by a proximal bendable zone 4 that forms a controller and a distal bendable zone 5 that forms an effector, whereby:

the wall of the tubular member 1 in a bend-resistive zone 6 comprises a structure that is a plurality of longitudinal slits 7, forming a plurality of longitudinal strips 8, 8', the wall of the tubular member 1 in a proximal bendable zone 4 and a distal bendable zone 5 comprises a structure that is a plurality of longitudinal wires 9, 9', 10, 10', at least one strip 8 is in connection with a wire 9 in the proximal bendable zone 4 and a wire 10 in the distal bendable zone 5, such that translation by said wire 9 in the controller is transmitted via the strip 8 to said wire 10 in the effector, a proximal annular region 11 of the tubular member 1, proximal to the proximal bendable zone 4, a distal annular region 12 of the tubular member 11 distal to the distal bendable zone 5.

Another embodiment, of the present invention is a hollow elongate tubular member 1 having a proximal end 2 and distal end 3, comprising:

a wall surface disposed between said proximal 2 and distal end 3, a proximal bendable zone 4 that forms a controller, a distal bendable zone 5 that forms an effector and flexes responsive to movements of the controller, and, a bend-resistive zone 6 between the aforementioned zones 4, 5 that transmits movements of the controller to the effector, whereby:

the wall of the tubular member in the bend-resistive zone 6 comprises a structure that is a plurality of longitudinal slits 7, flanking a plurality of longitudinal strips 8, 8', the wall of the tubular member in proximal bendable zone 4 comprises a structure that is a plurality of longitudinal proximal wires 9, 9', the wall of the tubular member in distal bendable zone 5 comprises a structure that is a plurality of longitudinal distal wires 10, 10', at least one strip 8 is in connection with a wire 9 in the proximal bendable zone 4 and a wire 10 in the distal bendable zone 5, such that translation by said wire 9 in the controller is transmitted via the strip 8 to said wire 10 in the effector, a proximal annular region 11 of the tubular member 1, is proximal to the proximal bendable zone 4, and a distal annular region 12 of the tubular member 11 is distal to the distal bendable zone 5.

The steering technology is formed in the wall of the tubular member 1 itself, thereby reducing significantly the wall thickness, and obviating the requirement of cables and associated technical difficulties with connecting, aligning and pre-tensioning cables cables. The steerable tube 100 is typically formed from a single, substantially solid-walled hollow elongate tubular member 1 which may be cut according to the invention, preferably using an accurate cutting system. Affixation techniques are not essential, and thus bulky joints typically associated with conventional tubes may be avoided, and do not conflict with a narrow profile. The invention thus provides a streamlined continuation of steering strips to the ends of the tube, whereby the risk of breakage is significantly reduced. Sterilization is facilitated since the parts are dismountable.

Alternatively the tubular member is formed by assembling one or more separately formed jig-sawed pieces.

Bendable Zones

A bendable zone 4, 5 is a region in which the hollow elongate tubular member 1 is able to flex i.e. diverge from a longitudinal axis (A-A') of the bend-resistive zone 6. Preferably, the tubular member 1 is able to bend in any direction providing left, right, forward, backwards movements, and movements in between to the effector. The construction of the device may alternatively allow a restricted movement, for example, when a plurality of wires 9, 9', 10, 10' is connected to the same strip 8 providing, for instance, only a left and right movement by the bendable zone 4, 5.

According to one aspect of the invention, the wall of the tubular member in proximal bendable zone 4 comprises a structure that is a plurality of longitudinal proximal wires 9, 9' separated by longitudinal apertures 13, 13'. In this instance, flexibility in the bendable zones 4, 5 is achieved in principal by the longitudinal apertures 13, 13', 14, 14' in the wall of the elongate tubular member 1 which are shaped to provide a plurality of narrow wires 9, 9', 10, 10'. The apertures and hence wires are preferably evenly arranged around the circumference of the elongate tubular member, thereby forming a tubular wall that can bend without kinking. The number of wires 9, 9', 10, 10' is preferably 1, 2, 3, 4, 5, 6, 7, 8 or more. The number of apertures 13, 13', 14, 14' is preferably 2, 3, 4, 5, 6, 7, 8 or more.

The skilled person will appreciate that the bendable zones 4, 5 may still have the requisite bending properties even when longitudinal apertures 13, 13' are absent. In such case, a wire 9, 9', 10, 10' will have the same circumferential width as a strip 8 and may be an extension of a strip 8. Typically an outer sheath 20 will contribute to the differential flexibility in the bendable zones 4, 5 and bend resistive zone 6 as explained elsewhere herein. The wires 9, 9', 10, 10' are preferably evenly arranged around the circumference of the elongate tubular member, thereby forming a tubular wall. The number of wires 9, 9', 10, 10' is preferably 1, 2, 3, 4, 5, 6, 7, 8 or more.

A wire 9, 9', 10, 10' in a bendable zone 4, 5 may be more narrow than a strip 8 in the bend-resistive zone 6, and consequently is able to adopt more flexibility which contributes to the bending property of the zones. Alternatively, a wire 9, 9', 10, 10' in a bendable zone 4, 5 may be the same width as a strip 8 in the bend-resistive zone 6 as explained herein. According to one aspect of the invention, the circumferential width of a wire 9, 9', 10, 10' (WPW or WDW) in the narrowest part, is 0%, 1%, 2%, 3%, 4%, 5%, 10%, 15%, 20%, 25%, 30%, 35%, 40%, 45%, 50%, 55%, 60%, 65%, 70%, 75%, 80%, 90% less than the circumferential width of a strip 8, (WS) in the narrowest part, or a value in the range between any two of the aforementioned values. Preferably the value of WPW or WDW is between 50% and 80%, or between 0% and 80% less than the value of WS, though in practice the precise percentage will depend on the final diameter of the elongate tubular member and material used.

Figure 5:
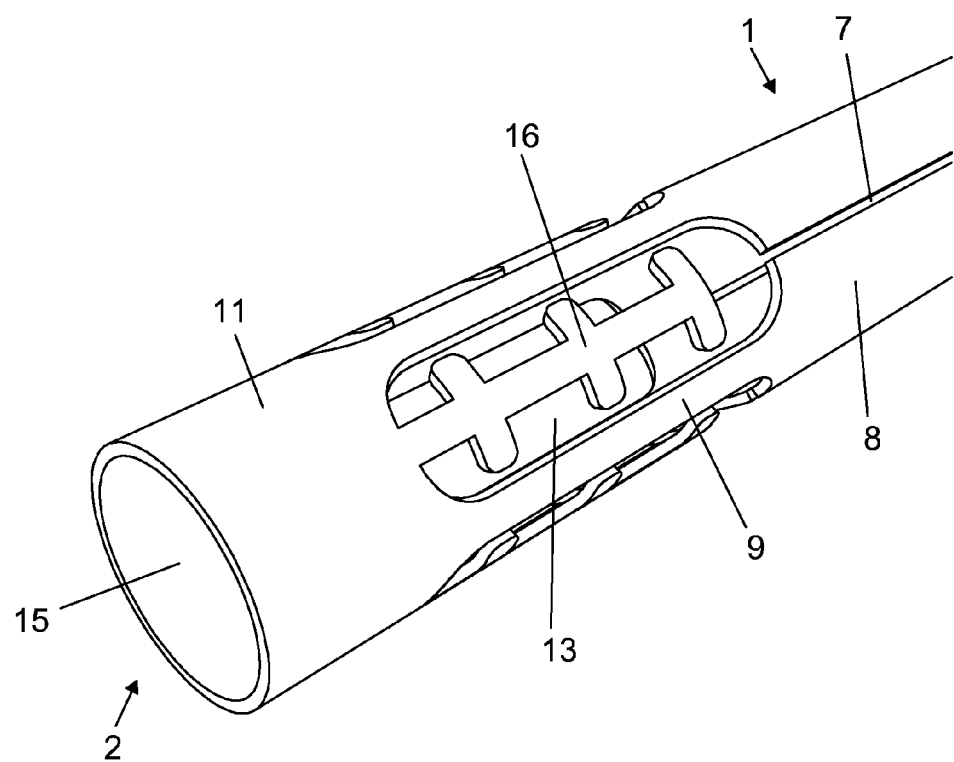
FIG. 5 depicts a perspective view of the proximal bendable zone disposed with a spacer in the apertures.

According to one aspect of the invention, the steerable tube has one or more spacers configured to maintain distance between the wires. If a wire 9, 9', 10, 10' is narrowed extensively, for example, when using only three strips 8, the use of a spacer 16 (see FIG. 5) in one or more of the apertures 13, 13', 14, 14' between the narrow wires 9, 9', 10, 10' may provide smoother movements by reducing buckling of the wires, though it is not essential. It will be appreciated that a spacer may be curved to match the cylindrical curvature of the elongate tubular member 1.

The spacer 16 may be attached to the annular region 11, 12. Parts of the wall left behind during the laser-cutting can create these fixed spacers.

Alternatively, spacing between the wires may be maintained by employing one or more spacers on a wire 9, in fixed attachment thereto, configured for slidable contact with an adjacent wire 9' thereby maintaining its distance therefrom.

According to one aspect of the invention, the aforementioned wire-bound spacer is formed by one or more bends in the wire 9. The wire so bent 17, 17' may have a undulating shape as shown, for example in FIG. 6A. The undulations, having a concave (upper) and convex (lower) part, are in slidable contact with straight (non-bent) wires 9, 9' adjacent on both sides. It is within the scope of the invention that the bent wire has a concave or convex undulation (not shown), and the undulation is in slidable contact with a straight region of an adjacent wire on one side.

Figure 6:
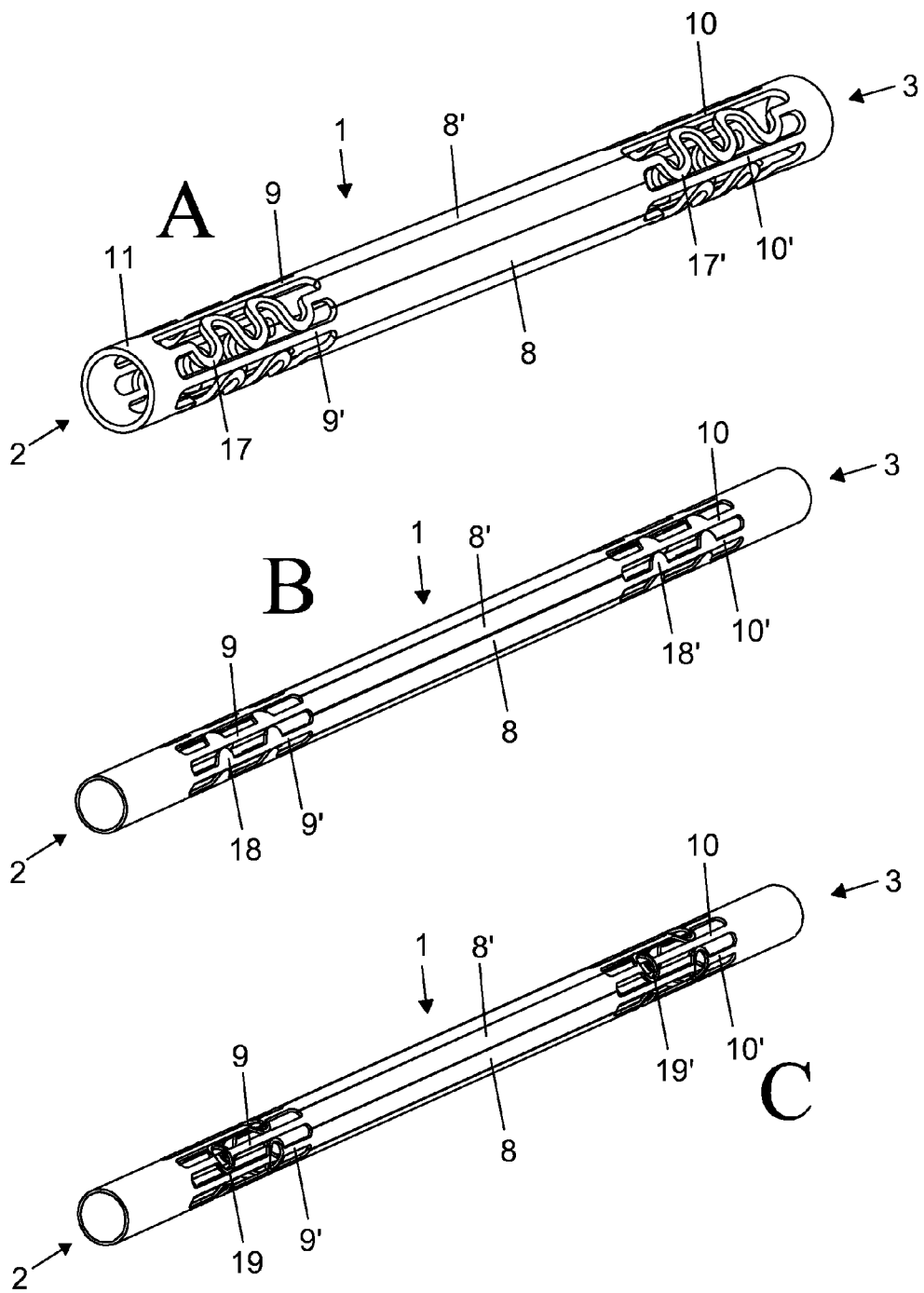
FIG. 6A to 6C depicts alternative configurations for a spacing means to stabilize the wires.

The number of undulations per wire, where present, may be 1, 2, 3, 4, 5, 6, 7, 8, 9, 10 or more, depending on the size of the undulation and the length of the wire. For example, the bent wire 17, 17' depicted in FIG. 6A is disposed with 5 undulations.

Alternatively or in addition, an aforementioned wire-bound spacer is formed from a tooth-shaped protrusion in fixed attachment to a wire, configured to slidably contact an adjacent wire. A tooth-shaped spacer 18, 18", may be attached in either a concave or convex relation to the longitudinal length of the wire, and is in slidable contact a straight region of an adjacent wire on one side as shown, for example, in FIG. 6B. Alternatively, two or more tooth-shaped spacers may be attached one in a concave and another in a convex relation to the longitudinal length of the wire, and is in slidable contact a straight region of adjacent wires on both sides (not shown). Said adjacent wires may be straight, or may be disposed with one or more teeth. The number of tooth-shaped per wire, where present, may be 1, 2, 3, 4, 5, 6, 7, 8, 9, 10 or more, depending on the size of the undulation and the length of the wire. For example, the wire 9, 9' depicted in FIG. 6B is disposed with 2 undulations.

Alternatively or in addition, an aforementioned wire-bound spacer may be formed from the structure arising when the above-mentioned concave and convex undulations are superimposed at the same position on the wire, i.e. a ring-shaped spacer is formed that is in slidable contact with a straight region of adjacent wires 9, 9' on both sides. Said adjacent wires may be straight, or may be disposed with one or more ring-shaped spacers. Said ring shaped spacers 19, 19' may be formed from a hollow ring as depicted in FIG. 6C, or from a solid ring (not shown). The ring may be circular or oval. The number of rings per wire, where present, may be 1, 2, 3, 4, 5, 6, 7, 8, 9, 10 or more, depending on the size of the ring and the length of the wire. For example, the wire 9, 9' depicted in FIG. 6C is disposed with 1 undulation.

It will be appreciated from the above that the invention includes any other cutting patterns to maintain spacing between the wires within its scope.

It is an option that one or more of the wires 9, 9', 10, 10' in the bendable zones 4, 5 is thinned i.e. reduced in material thickness (TP or TD) to provide increased flexibility. Thinning may be achieved by chemical etching or other techniques known in the art. It is an option that one or more of the wires 9, 9', 10, 10' in the bendable zones 4, 5 is rounded to remove sharp corners. Rounding may be achieved by electropolishing or other techniques known in the art.

The wires 9, 9', 10, 10' that provide flexibility need not be linear and aligned with the longitudinal (A-A') axis in an unflexed state as shown in the FIG. 4A, for example. One or more of the wires 9, 9', 10, 10' may be aligned with or inclined to the longitudinal (A-A') axis of the hollow elongate tubular member 1. One or more of the wires 9, 9', 10, 10' may be at least partly linear, though other patterns are envisaged, for example, wires that are undulating 17 (FIG. 6A), or curved shaped. or any suitable pattern as seen, for instance, in stent production are all within the scope of the invention. As mentioned earlier, one or more wires may be disposed with tooth-shaped spacers 18 (FIG. 6B), or disposed with ring-shaped spacers 19 (FIG. 6C).

Figure 16:
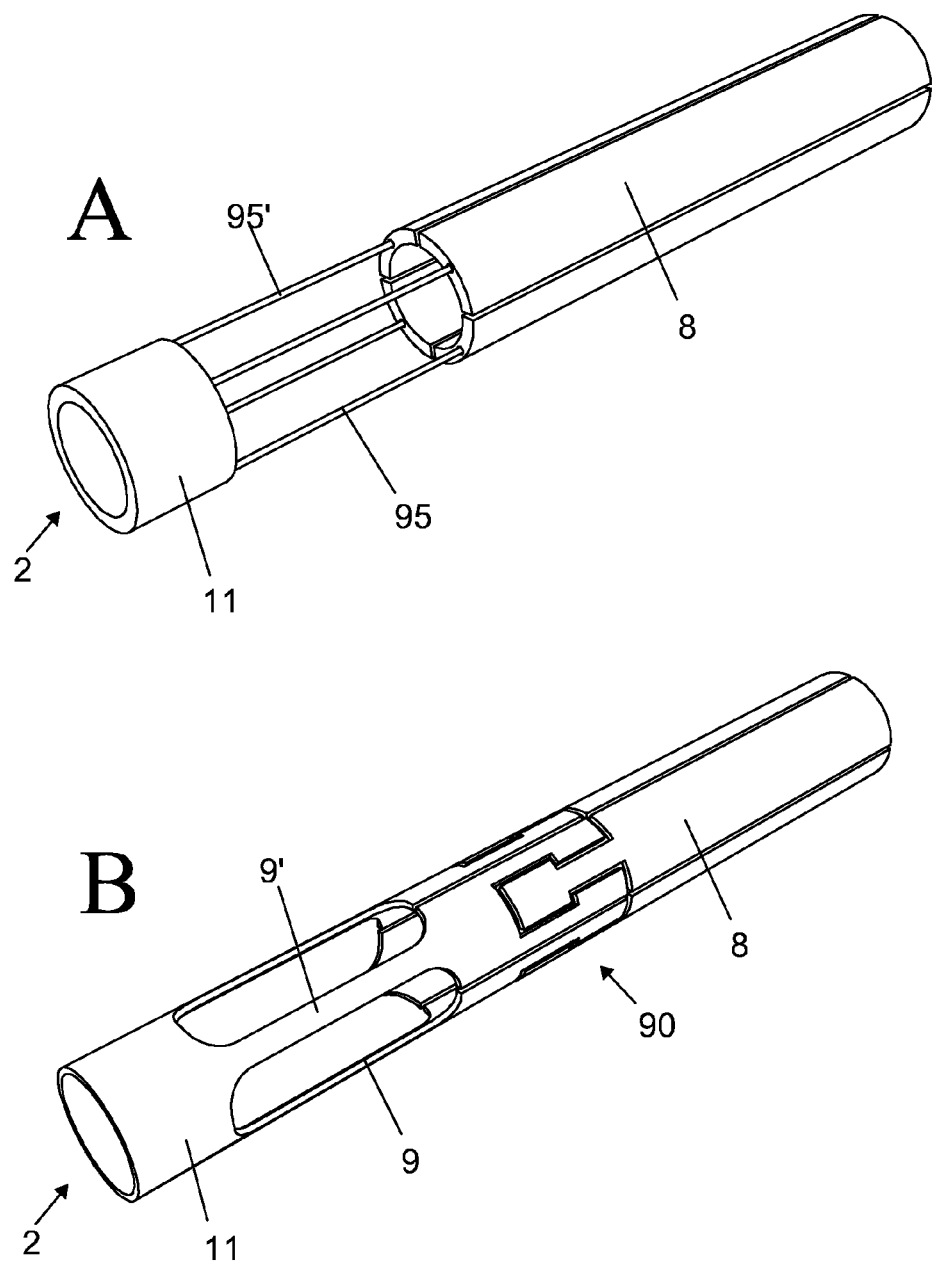
FIG. 16A illustrate a perspective view of the proximal bendable zone, where the strips are joined to rod-shaped wires, which wires are made from a different material (e.g. Nitinol) from the strips (e.g. made from stainless steel).
FIG. 16B illustrate a perspective view of the proximal bendable zone, where the strips are joined to the wires by a joint, which wires are made from a different material from the strips.

According to one aspect of the invention, a wire 9 is a solid nitinol rod 95, 95' inserted or laser welded in a small burr hole in the strip 8 and annular region 11 (FIG. 16A). According to another aspect of the invention, a wire 9 is made from a different material to the adjoining strip 8, and is attached to the strip by joint 90 (FIG. 16B). The joint 90 is preferably a dove-tail joint, or the like.

Controller

When the controller (proximal bendable zone 4) is flexed, its movements are transmitted via the bend-resistive zone 6 to the effector (distal bendable zone 5) which flexes responsive to movements of the controller. The controller may be manually manipulated or it can be coupled to mechanical movement means (e.g. electromechanical). In the latter case, the movements of the controller may be servomechanically actuated, for example, by use of a telesurgical system. Electromechanical movement may also alternatively or additionally be realised by the use of linear motors that operate on the strips 8 of the tubular member 1 as described elsewhere herein.

Increased bending-couple or leverage in the proximal bendable zone 4 (controller) can be achieved by a progressive increase of the tubular member 1 diameter towards the proximal end 2 in comparison to the rest of the elongate tubular member. According to one aspect of the invention, the diameter of the tube in the proximal bendable zone 4 is 5%, 10%, 15%, 20%, 25%, 30%, 50%, 100%, 200%, 300%, 400%, 500%, 600%, 700%, 800%, 900%, 1000%, 2000% or more, greater than the diameter of the tube in the remainder of the tube when comparing the maximum diameter of the proximal bendable zone 4 with the minimum diameter of the remainder of the tube, or a value in the range between any two of the aforementioned values.

Alternatively the proximal end could be fixed to a gimbal-plate or gimbal-ball. This increased bending-couple might be of interested for the mostly long endovascular catheters in which more force-lost is seen due to torturous path of the tube in the vascular structures.

As mentioned elsewhere, the proximal bendable zone 4 (controller) may be coupled to a mechanical movement means, particularly to an electromechanical means. One embodiment of the invention, is an electromechanical controller for a steerable tube 100 of the invention comprising a holder configured for dismountably attaching a steerable tube of the invention, and an electromechanical actuator configured to controllably move the proximal bendable zone 4 (controller) within its range of movement, and optionally to rotate the steerable tube around its central axis. The holder preferably attaches in the region of the bend-resistive zone 6. The attachment is dismountable, meaning that steerable tubes can be interchanged with the same controller; this has the advantage that a steerable tube may be removed for sterilization or replaced where necessary without need for changing the electromechanical controller. The electromechanical actuator may comprise two or more servo motors, arranged for two or three axis control around a pivotal point of the proximal bendable zone 4. The skilled person will be able to implement suitable working configuration of the electromechanical controller based on the guidance herein.

Effector

The effector (distal bendable zone 5) moves responsive to movements of the controller, typically in mirrored manner. For example, a forward movement by the controller will result in a backward movement by the effector and vice versa.

The effector of the invention provides an excellent steering stability as a result of several factors. A large bending moment is available since the wires terminate at a far lateral offset relative to the tube centerline. Further, both pulling and pushing are transmitted to the effector, which forces cooperate to provide both a large net mechanical force and exquisite control. The effector has a high bending stiffness to limit undesirable deflections such as S-shape bending and has a high torsional stiffness. The effector can withstand severe lateral loads and allows axial rotation (transmission of torque) even in a bent position. This is particularly of importance for example, if it is required to bring together the jaws of a scissor perpendicular to a blood vessel.

The elongate tubular member 1 of the invention is hollow, thus it may act as a lumen providing a passage from the proximal 2 to the distal 3 tip of the elongate tubular member. The effector, therefore, is provided with the lumen which can receive operating wires or fluids when the lumen is lined with a water impermeable substance. Furthermore, the effector may be adapted to support one or more additional instruments for remote operation such as clamps, graspers, scissors, staplers, aspiration catheter, laser fibers and needle holders. The adaptation of the effector will be readily understood by the skilled artisan, and is discussed further below.

Bend Resistive Zone

The bend-resistive zone 6 connects the proximal bendable zone 4 with the distal bendable zone 5 and transmits movements of the controller to the effector. The wall of the tubular member in the bend-resistive zone 6 comprises a structure that is a plurality of longitudinal slits 7, that flank a plurality of longitudinal strips 8, 8'. The slits cut across the bend-resistive zone 6 in the longitudinal (A-A') direction allowing each strip to slide independently of the adjacent strip. In transmitting forces, the strips exhibit negligible compliance and thus efficient use is made of almost the complete wall structure. It will be apparent that when the strips are aligned adjacently to form the hollow elongate tubular member 1, the flexibility of the bend-resistive zone 6 is reduced. The bend-resistive zone 6 is considerably less flexible than the bendable zones 4, 5. The flexibility may be attributable, for example, to the presence of no or few apertures which would otherwise provide flexibility. Alternatively, the inner lining or outer sheath in the bend resistive zone may be less flexible than in the bendable zone. The longitudinal slits 7 and hence longitudinal strips 8, 8' are preferably evenly arranged around the circumference of the elongate tubular member. The number of longitudinal strips 8, 8' is preferably 2, 3, 4, 5, 6, 7, 8 or more. The number of longitudinal slits 7 is preferably 2, 3, 4, 5, 6, 7, 8 or more.

The degree of bendability in the bend-resistive zone 6 while being less than that in the bendable zones 4, 5 will depend on the number of longitudinal strips 8, 8' or slits 7, the material used to form the elongate tubular member 1 and its thickness.

As mentioned already, at least one strip 8 is in mechanical connection with a wire 9 in the proximal bendable zone 4 and a wire 10 in the distal bendable zone 5, such that translation by said wire 9 in the controller is transmitted via the strip 8 to said wire 10 in the effector. The connection is generally rigid. The number of wires connected to a single strip is typically two—one proximal wire 9, 9' and one distal wire 10, 10'—however, it is not necessarily limited to this number. It is envisaged that more than two wires can be connect to a single strip 8 in order to provide, for example, a restricted movement which can be desirable in applications where the full range of motion might otherwise lead to damage to the object being inspected or operated on.

As mentioned above, the circumferential width of a wire 9, 9', 10, 10' (WPW or WDW) of a bendable zone, in the narrowest part, is 0%, 1%, 2%, 3%, 4%, 5%, 10%, 15%, 20%, 25%, 30%, 35%, 40%, 45%, 50%, 55%, 60%, 65%, 70%, 75%, 80%, 90% less than the circumferential width of a strip 8, (WS), of the bend-resistive zone 6, in the narrowest part, or a value in the range between any two of the aforementioned values. Preferably the value of WPW or WDW is between 50 and 80%, or between 0 and 80% less than the value of WS, though in practice the precise percentage will depend on the final diameter of the elongate tubular member and material used.

Figure 4:
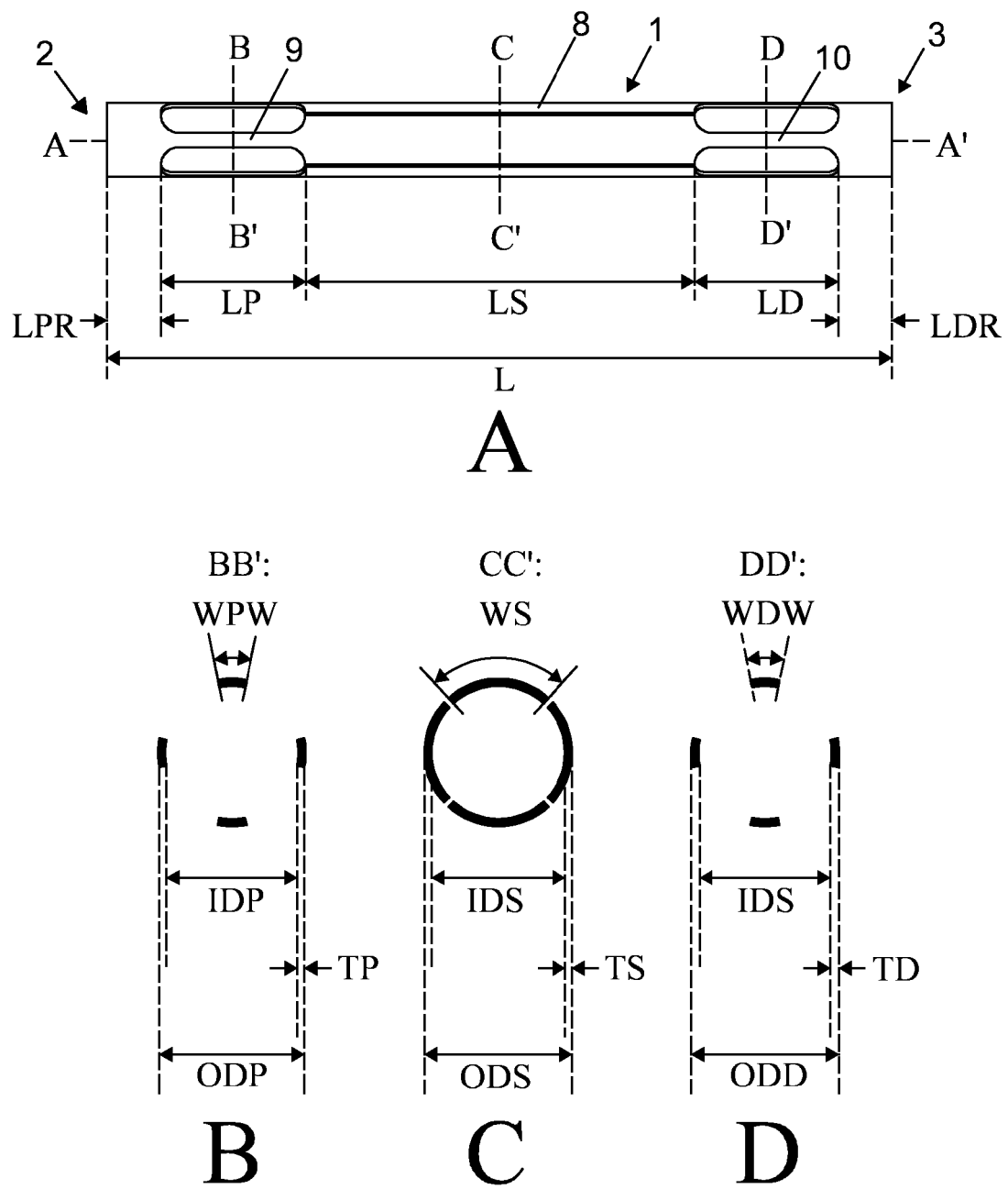
FIG. 4A illustrates the dimensions of a steerable tube of the present invention.
FIGS. 4B to 4D illustrates the dimensions of the transverse cross sections.

The longitudinal slits 7 and hence longitudinal strips 8, 8' need not be linear and aligned with the longitudinal (A-A') axis as shown in, for example, FIG. 4. One or more of the longitudinal strips 8, 8' may be aligned or inclined to a longitudinal (A-A') axis of the hollow elongate tubular member 1. One or more of the longitudinal strips 8, 8' may be at least partly linear, though other patterns are envisaged, for example, spiral strips, or any suitable pattern as seen, for instance, in stent production.

According to one aspect of the invention, the bend resistive zone comprises a braking mechanism, configured, when activated to prevent slidable movements by the strips 8, 8'. When the brake is applied, the position of the distal bendable zone 5 is fixed; i.e. it becomes resistive to force applied thereto. The brake may take any form, for example, a compressible annular ring having an inner diameter that varies according to the degree of compression. The inner circumference of the ring applies pressure to the strips 8, 8' of the elongate tubular member 1 when the ring is compressed along its central axis.

Figure 9:
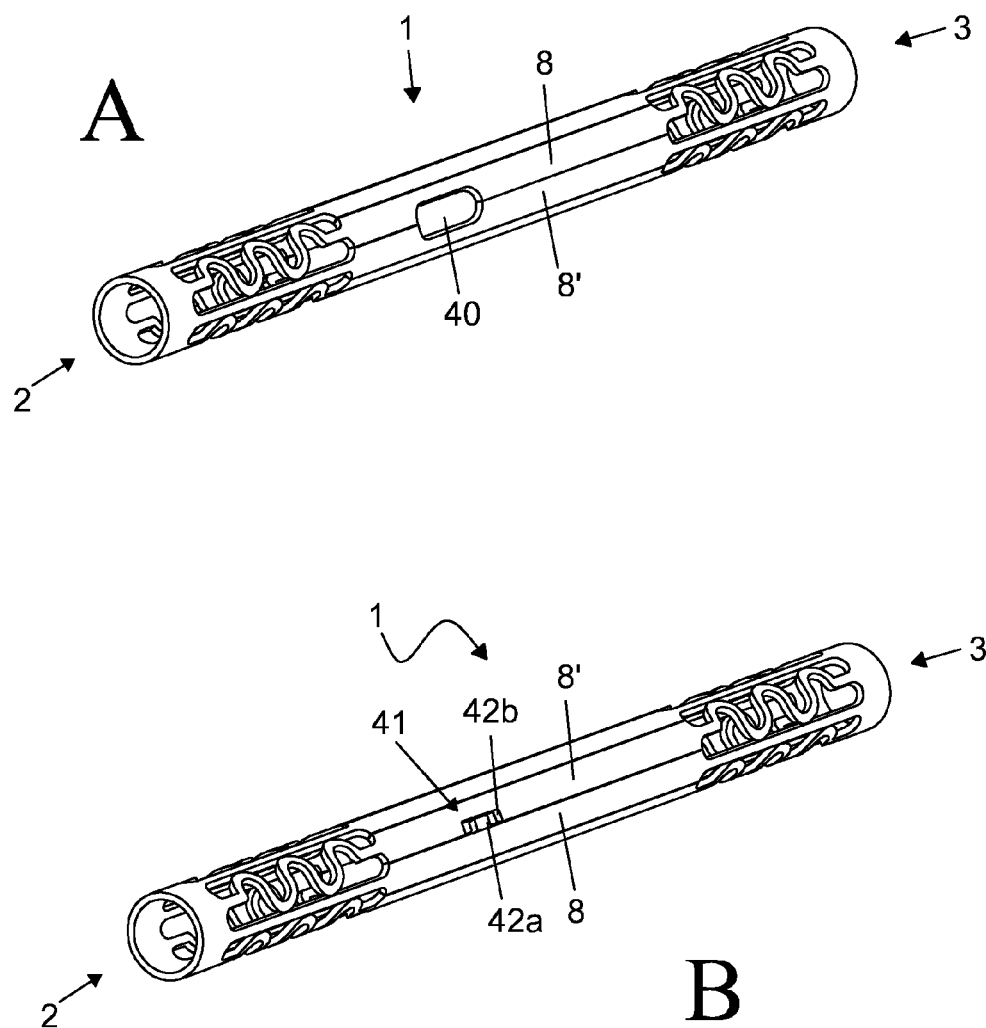
FIG. 9A depicts a side port created by cutting of apertures between two adjacent strips to allow lateral exit of, for example, wires, electrical cables or aspiration ducts.
FIG. 9B depicts a limit stop mechanism that controls the extent of slidable movement by two strips, which limits stop is formed from a tooth fixed to one strip in slidable connection with a reciprocating notch in an adjacent strip that limits, for instance, the angle of motion of the instrument.

According to one aspect of the invention, the elongate tubular member 1 comprises a side port 40 created by cutting an aperture between two adjacent strips 8, 8' as shown, for example, in FIG. 9A. The aperture is dimensioned to maintain integrity of the strip in the longitudinal direction. The width of the region of a strip that form said aperture may be less than the width, WS (FIG. 4C), of a strip. The side port 40 allows side access to a hollow of the steerable tube 100 or inner lining 50. The side port 40 may allow exit of wires, electrical cables or aspiration ducts from a hollow of the elongate tubular member 1 or inner lining 50. Alternatively or in addition, side port 40 may be in fluid connection with the distal 3 tip of the steerable tube 100, allowing the introduction of liquids (e.g. medicaments, washing solutions, contrast agents) and/or aspiration in the vicinity of the distal 3 tip. The skilled artisan will appreciate that any inner lining 50 or outer sheath 20 will be disposed with a corresponding aperture, aligned with the aperture formed in the elongate tubular member 1.

According to one aspect of the invention, the elongate tubular member 1 incorporates a limit stop mechanism 41 that controls the extent of relative slidable movement between two strips 8, 8'. In a preferred embodiment, depicted in FIG. 9B, the limit stop 41 is formed from a tooth 42a fixed to the edge of one strip 8 in slidable connection with a reciprocating notch or crenellation 42b in an edge of an adjacent strip 8'. Movement of the tooth 42a within the notch 42b is limited when the tooth 42a contacts the distal or proximal notch 42b edges at the extreme ranges of movement. The limit stop mechanism 41 is preferably located within the bend resistive zone 6. The effect of the limit stop is to restrict, for instance, the extent to which the instrument flexes i.e. the maximum angle of flexure.

According to one aspect of the invention, the steerable tube 100 further comprises a rotation limiting mechanism 44, 44' (FIGS. 10A and B) formed from a radial protrusion (known as a keel herein) 45a, 45'a present in one coaxially rotatable element (e.g. the elongate tubular member 1) in longitudinal slidable connection with a reciprocating slot 45b, 45'b in another coaxially rotatable element (e.g. outer sheath 20 or inner lining 50) of the steerable tube 100 configured to reduce or prevent unwarranted revolute movement by the elongate tubular member 1 relative to the outer sheath 20 or inner lining 50. While in the above example the keel 45a, 45'a is present in the elongate tubular member 1 and the slot is present in the outer sheath 20 or inner lining 50, it is within the scope of the invention that a slot may be present on the elongate tubular member 1 and the keel present on the outer sheath 20 or inner lining 50. The rotation limiting mechanism 44, 44' is preferably located within the bend resistive zone 6. The rotation limiting mechanism 44, 44' is of importance when lateral forces are applied to the tip of the instrument in a bent position, which would otherwise cause the tip to move and lose its placement.

Figure 10:
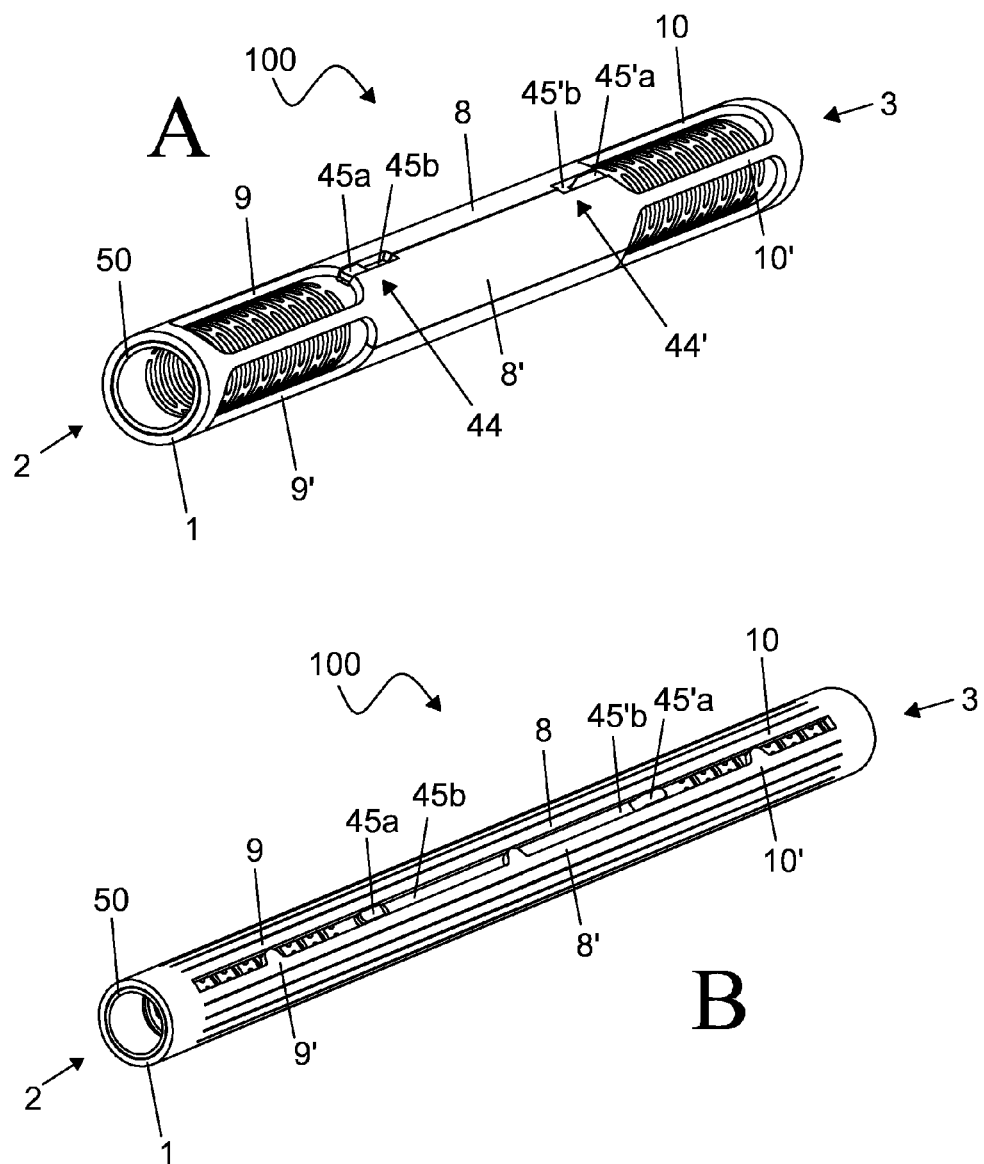
FIG. 10A. depicts an example of a rotation stop formed from a radial protrusion (a keel) fixed to the inner tube, in slidable connection with a reciprocating slot formed between two strips of the elongate tubular member, which rotation stop decreases the torsion of steerable tube around the central axis relative to the inner tube.
FIG. 10B. depicts a further example of a rotation stop formed from a radial protrusion (keel) fixed to the inner tube, in slidable connection with a reciprocating slot formed from a remove strip of the elongate tubular member, which rotation stop decreases torsion of strips around the central axis relative to the inner tube.

The slot 45b, 45'b may be any shape, depending on the desired movement at the distal end 3, though it should be narrow and engage with the keel 45a, 45'a sufficiently prevent free rotation of the distal bendable zone 5 upon the application of a torque thereto. Preferably, the slot 45b, 45'b is straight and parallel with the longitudinal axis (A-A') of the bend-resistive zone. According to one aspect of the invention a slot is formed along at least part of the length of a strip 8, 8'. According to another aspect of the invention a slot is formed along at least part of the length between of two adjacent strips 8, 8'. According to another aspect of the invention a slot is formed form a strip of the elongate tubular member 1 disconnected from the wires or annular regions as shown in FIG. 10B.

Figure 11:
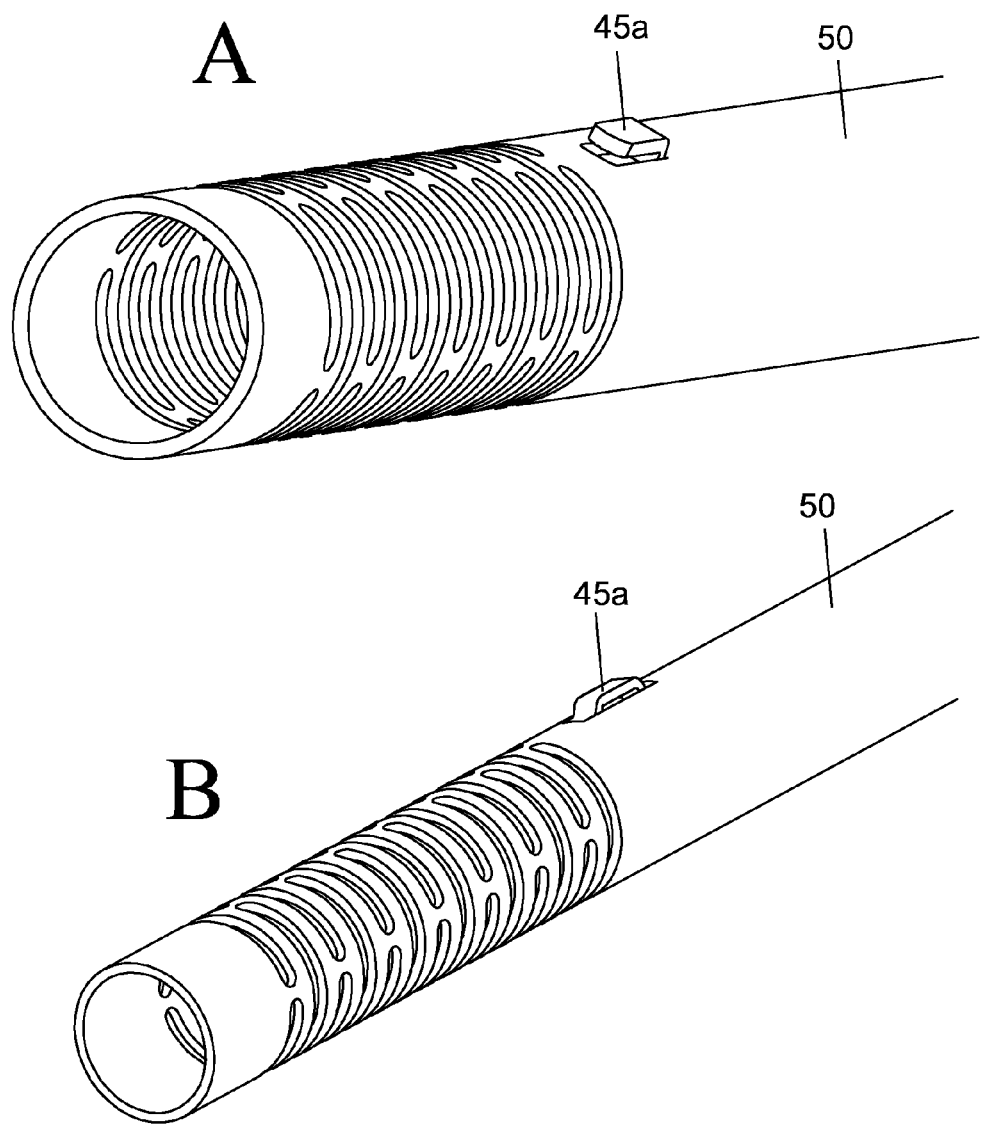
FIGS. 11A and 11B depict the keel of FIGS. 10A and 10B in a detailed view.
Figure 12:
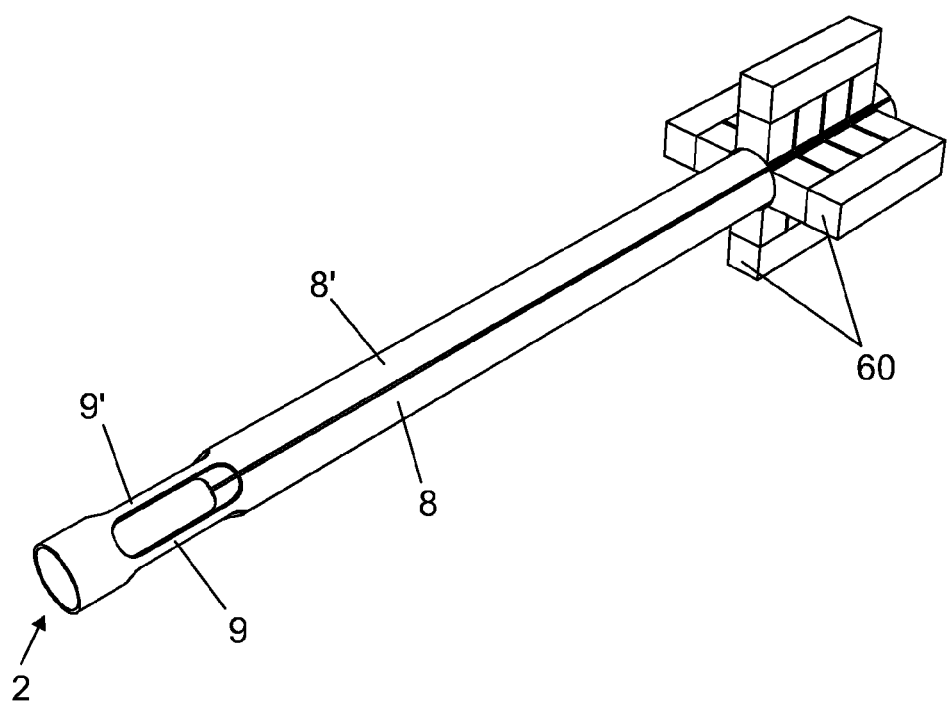
FIG. 12 illustrates a perspective view of the distal bendable zone, where four strips are provided with piezomotors.

Should a rotation movement be desired at the distal bendable zone 5, the slot may be spiral. The spiral may permit an anti-clockwise or clockwise rotation simultaneous with flexure of the distal bendable zone 5. The keel may be, but not necessarily, considerably shorter than the length of a strip. FIGS. 10A and 10B depicts a steerable tube 100 disposed with a rotation limiter 44, 44' in which the keel 45a, 45'a is disposed on the inner lining 50 and the slot 45b, 45'b is disposed on the elongate tubular member 1. FIGS. 11A and 11B show in detail the keel 45a of the inner lining 50 disposed within the elongate tubular member 1 depicted in FIGS. 10A and 10B respectively. Preferably there are 1, 2, 3, 4, 5, 6, 7, 8, 9 or 10 or more keel and slot pairs along the same linear path, depending on the length of the keel and of the steerable tube 1. Preferably there is at least one keel every 20, 30, 45, 60, 72, 90, 120, or 180 degrees.

Figure 1:
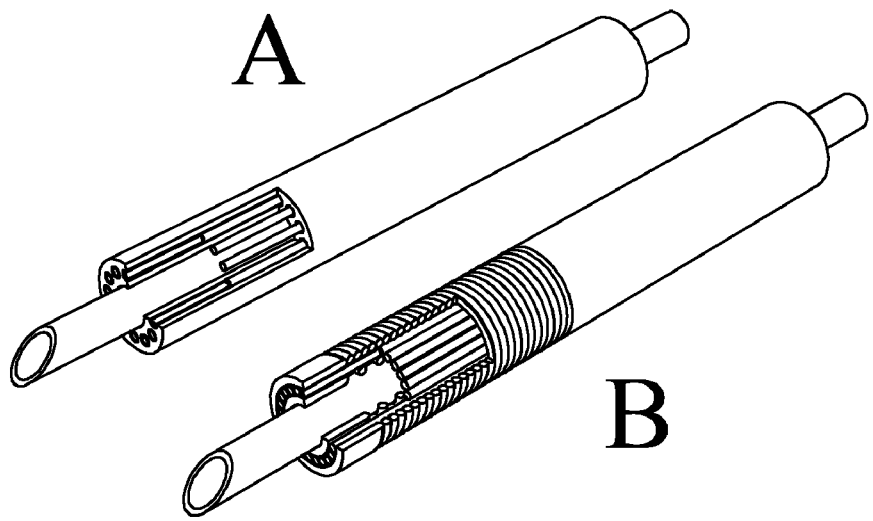
FIGS. 1A and 1B show cut away sections devices in the art comprising a plurality of cables fed through guide sleeves (FIG. 1A) or disposed side by side (FIG. 1B).
FIGS. 1C and 1D show transverse sections across the devices of the art shown in FIGS. 1A and 1B respectively, together with indications of outer (OD) and inner (ID) tube diameters.
Figure 1:
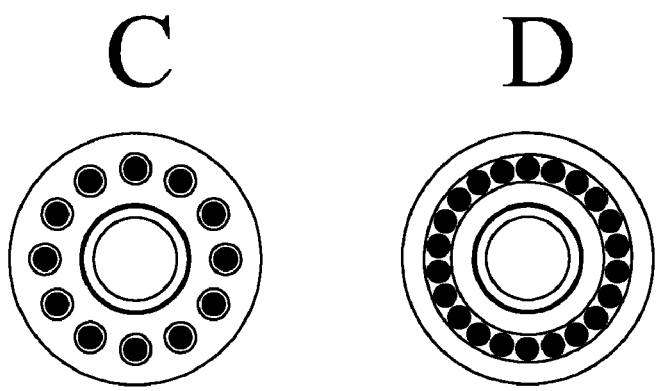

It is within the scope of the invention that the above-mentioned rotation limiter 44, 44' is applied to any device, operating along similar principles, whereby forces are transmitted by a transmission means (e.g. strips, rods or cables) covered with an independently-rotatable inner or outer lining. For example, one or more cables of FIG. 1D may be disposed with a keel that is in longitudinal slidable connection with a reciprocating slot in an outer sheath or inner lining of the steerable tube, which arrangement is configured to reduce or prevent unwarranted revolute movement by the cylinder of cables. One embodiment of the invention is rotation limiting mechanism for a steerable tube comprising a plurality of cables arranged in a hollow cylinder, circumferentially flanked by an inner and/or outer tubular support whereby the cylindrically arranged cables, and one of the inner and outer tubular supports are coaxially rotatable elements, which rotation limiting mechanism is formed from a radial protrusion present in any one coaxially rotatable element, in longitudinal slidable connection with a reciprocating slot in another coaxially rotatable element of the steerable tube configured to reduce or prevent co-axial rotation by the cylindrically arranged cables relative to the inner or outer tubular support.

Figure 8:
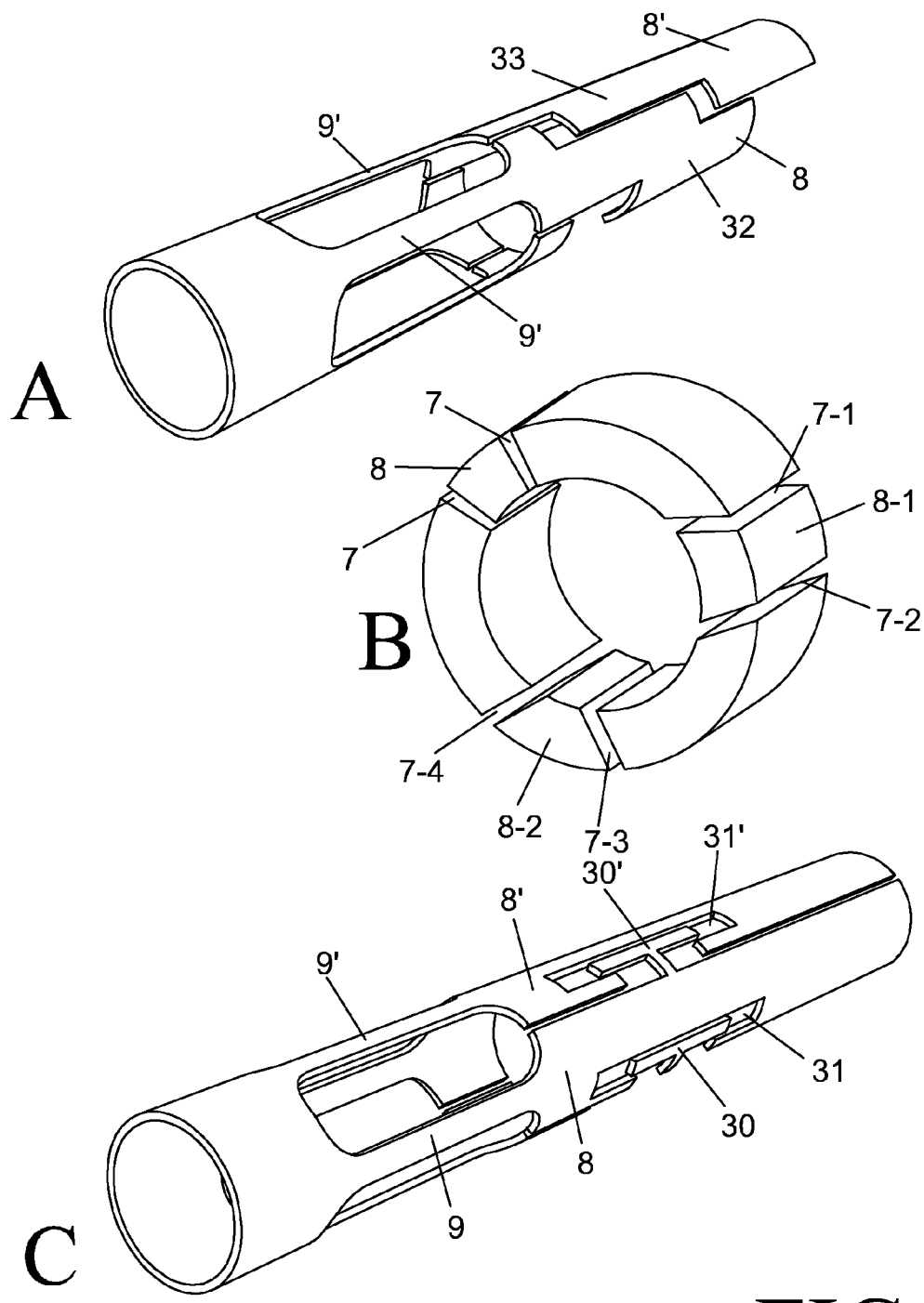
FIGS. 8A to 8C depicts perspective views where the strips are provided with additional circumferential cuts (FIG. 8A), and examples of radial and non-radial slits (FIG. 8B) or an interconnection (FIG. 8C).

According to one aspect of the invention, the controller may operated by the use of linear motors such as piezomotors (e.g. Piezo LEGS®). Such piezomotors 60 may be arranged radially around the strips (inside or outside, parallel or sequential) of the tubular member 1 (FIG. 8). Piezomotors 60 may be arranged around the inside or outside of the tubular member 1 (FIG. 8). There may be one or more (e.g. 1, 2, 3, 4, 5, 6, 7, 8, 9, 10 or more) piezomotors 60 per strip 8. The movement part of a piezomotor 60 is in mechanical contact with a strip 8, while a frame of the piezomotor 60 may be attached to a static element on the steerable tube, such as an outer sheath 20 (not shown). According to one aspect of the invention, the strips may be actuated using Flexinol®. Flexinol® actuators contract, in a similar manner to muscles, by a shortening or elongation of approximately 4-5%; thus they contract when they are on and relax when they are "off". Movement of the strips may be achieved by arranging insulating strips placed between the actuating strips 8 of the hollow member 1. Advantageously, the use of linear motors allow a plurality of motorized steerable tubes to be connected, end to end, that offers a snake like tube (FIG. 13B) having a wide range of motion at the effector end. It is not essential that the proximal bendable zone 4 is present in such a configuration. When the steerable tubes 100 are joined by motorized revolute joints, the range of motion is further enhanced. One embodiment of the invention is a composite steerable tube formed from two or more (e.g. 2, 3, 4, 5, 6, 7, 8, 10 or more) motorised steerable tubes tandemly arranged, and connected by rigid or revolute joints. One embodiment of the invention is a composite steerable tube formed from two or more (e.g. 2, 3, 4, 5, 6, 7, 8, 10 or more) motorised steerable tubes devoid of the proximal bendable zone 4 and proximal annular region 11 tandemly arranged, and connected by rigid or revolute joints.

Using a more complex cutting pattern, strips 8, 8' are within the scope of the invention whereby one or more of the longitudinal strips 8, 8' are held together (interlocked) using interconnections (FIG. 8C), non-longitudinal slits (FIG. 8A), non-radial slits (FIG. 8B) or longitudinal spiral cuts. In this constellation, the inner and outer coverings may be, but not necessarily, omitted. In this way, issues of sterilization, concerning access of steam to all areas and tubes, can be circumvented. It is noted that another way to overcome problems with sterilization is to make the steerable tube and any covering or lining perforated and/or dismountable.

Where a non-radial slit is employed (FIG. 8B), the slit diverges from the radius of the elongate tubular member. FIG. 8B depict the profile of slits taken in transverse (C-C') cross-section across the bend-resistive zone. It is noted, the distance between respective strips is exaggerated; in practice the strips are in sliding contact. Normally, the slit 7, 7' converges with the radius. When non-radial slits are used, the slits 7-1, 7-2 flanking a strip 8-1 may both diverge from the radius producing strips 8-1 with conical edges pointed outwards. Alternatively, when non-radial slits are used, the slits 7-3, 7-4 flanking a strip 8-2 may both diverge from the radius producing strips 8-2 with conical edges pointed inwards.

Annular Regions

Figure 14:
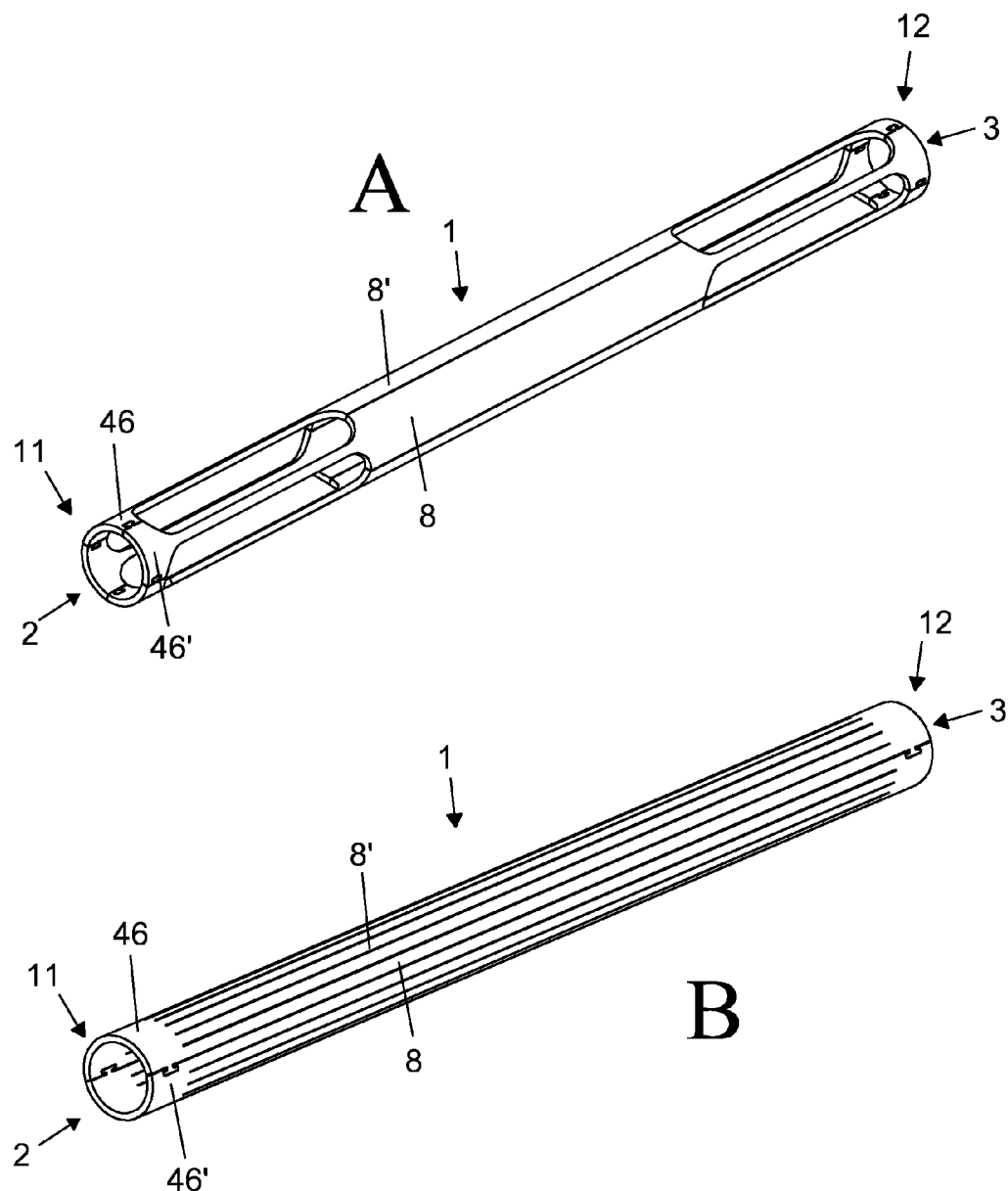
FIGS. 14A and 14B illustrate a steerable tube from the assembly of several parts to form an intact annular region for anchoring the wires.

Proximal to the proximal bendable zone 4 is a proximal annular region 11 of the hollow elongate tubular member 1. The proximal annular region 11 is adjacent and proximal to the proximal bendable zone 4. The proximal wires 9, 9' may be anchored to the proximal annular region 11. The proximal annular region may be circumferentially intact. In other words an intact region of the hollow elongate tubular member 1 may be uncut, having no slits or apertures, that would permit slidable movement within the proximal annular region 11. According to another aspect of the invention, the proximal annular region 11 is composed of one interlocking part that folds cylindrically to form a region of fixed circumferential shape. According to another aspect of the invention, the proximal annular region 11 is composed of two or more interlocking subparts 46, 46' (FIG. 14) that fits together cylindrically to form a region of fixed circumferential shape. The interlocking arrangement prevents relative slidable movement between the subparts. By virtue of this property the distal annular region 12 may have a constant width; the width does not substantially change when the proximal bendable zone 4 is flexed. The region may be ring-shaped. Wires 9, 9' extending from the proximal bendable zone 4 are rigidly attached to the proximal annular region 11. Typically the wires 9, 9' are evenly disposed around the circumference of the proximal annular region 11.

Similarly, distal to the distal bendable zone 5 is a distal annular region 12 of the hollow elongate tubular member 1. The distal annular region 12 is adjacent and distal to the distal bendable zone 5. The distal wires 10, 10' may be anchored to the distal annular region 12. The distal annular region may be circumferentially intact. In other words an intact region of the hollow elongate tubular member 1 may be uncut, having no slits or apertures that would permit slidable movement within the distal annular region 12. According to one aspect of the invention, the distal annular region 12 is composed of one interlocking part that folds cylindrically to form a region of fixed circumferential shape. According to another aspect of the invention, the distal annular region 12 is composed of two or more interlocking subparts (FIG. 14) that fit together cylindrically to form a region of fixed circumferential shape. The interlocking arrangement prevents relative slidable movement between the subparts. By virtue of this property, the distal annular region 12 may have a constant width; the width does not substantially change when the distal bendable zone 5 is flexed. The region may be ring-shaped. Wires 10, 10' extending from the distal bendable zone 5 are rigidly attached to the distal annular region 12. Typically the wires 10, 10' are evenly disposed around the circumference of the distal annular region 12.

The use of one or more interlocking parts to form the distal 12 and proximal 11 annular region allow an efficient construction of the elongate tubular member from one, two or more cut or molded parts (FIG. 14) i.e. without the requirement for cutting an intact tube. For example, the elongate tubular member may be formed from a flat sheet of material, having the appropriate elements, folded cylindrically and joined at the ends by virtue of interlocking circumferential joints in the distal 12 and proximal 11 annular regions to form a working elongate tubular member. Alternatively, the separate strips, wires and annular regions segments, optionally thinned at the bendable zones, can be assembled by virtue of interlocking circumferential joints in the distal 12 and proximal 11 annular regions.

The annular region 11, 12 can be of any longitudinal length depending on the application. It should be of sufficient length, however, to provide enough strength that avoids distortion of the annular region 11, 12 by tensional forces in the wires 9, 9', 10, 10'. Advantageously, it can be extended at the proximal end 2 in order to provide a greater leverage. Alternatively, it may be extended at the distal end 2 in order to provide a greater movement. Shorter distal annular region 12 will allow for a more precise angular control.

Materials of the Elongate Tubular Member

The elongate tubular member 1 can be made from any material which provides the requisite tensile and flexural properties. Suitable materials include stainless steel, cobalt-chromium, shape memory alloy such as Nitinol®, plastic, polymer, composites or other curable material. According to one aspect of the invention, the elongate tubular member 1 is made from the same material throughout, e.g. stainless steel or nitinol. According to one aspect of the invention, the elongate tubular member 1 is made from two or more different materials, for instance one material (e.g. stainless steel) in the bend-resistive zone 6 and another material (e.g. nitinol) in the bendable zones 4, 5. An example of such configuration is given in FIGS. 16A and 16B and described elsewhere herein. Alternatively different materials within the same tube can be used e.g. extrusion with two different materials.

Shape and Dimensions of the Elongate Tubular Member

The elongate tubular member 1 preferably has a cylindrical shape in the non-flexed stated, having a longitudinal axis A-A' (FIG. 4A). The dimensions discussed below refer to the elongate tubular member 1 in the non-flexed state, and refer to a measurement at a maximum point and not to an average.

The total length of the elongate tubular member 1, L, from the tip of the proximal end 2 to the tip of the distal end 3 will depend on the materials used in the elongate tubular member, considering its stretching and pushability properties, thickness and diameter. Theoretically, any length of elongate tubular member is possible providing sufficient leverage is provide by the proximal bendable zone, for example, by extending the length of the proximal annular region. In medical applications, a total length of up to 150 cm would be desirable (e.g. endovascular catheters) for, and it is envisaged for most applications needing fine control (e.g. surgery and endoscopes) that the total length will be between 10 cm and 40 cm.

The length of the proximal bendable zone LP will depend on the materials used in the elongate tubular member as mentioned above, and also the degree of movement, force and accuracy needed. In general, the higher the value of LP, the greater the force transmitted to the effector, though larger movements would be required. Values of LP are expect to be 1%, 1.25, 2%, 2.5%, 3%, 3.5%, 4, 4.5%, 5%, 6%, 7%, 8%, 9%, 10%, 15% or 20% the value of L. It is envisaged for most applications needing fine control that LP will be 0.5, 2 or 3 cm, preferably between 0.5 cm and 3 cm for a 40 cm elongate tubular member 1.

The length of the distal bendable zone LD will depend on the materials used in the elongate tubular member as mentioned above, and also the degree of movement, force and accuracy needed. In general, the higher the value of LD, the lower the force the end can apply, though the larger the movements. Values of LD are expect to be 1%, 1.25, 2%, 2.5%, 3%, 3.5%, 4, 4.5%, 5%, 6%, 7%, 8%, 9%, 10%, 15% or 20% A the value of L. It is envisaged for most applications needing fine control that LD will be 0.5, 2 or 3 cm, preferably between 0.5 cm and 3 cm for a 40 cm elongate tubular member 1.

The length of the proximal annular region LPR will depend on the materials used in the elongate tubular member as mentioned above, and the tensile (pulling) and compression (pushing) forces that the wires apply so as not to distort the proximal annular region. In general, the higher the value of LPR, the better the strength of the proximal annular region. In addition, a higher value of LPR will provide more leverage and hence more force to the effect. Values of LPR are expect to be 0.25, 0.5%, 0.625% 0.75%, 1%, 1.25, 2%, 2.5%, 3%, 3.5%, 4, 4.5%, 5%, 10% the value of L. It is envisaged for most applications where the proximal annular region will provide support and have no additional leverage that LDR will be between 0.5 cm and 5 cm for a 40 cm elongate tubular member 1.

The length of the distal annular region LDR will depend on the materials used in the elongate tubular member as mentioned above, and the tensile (pulling) and compression (pushing) forces that the wires apply so as not to distort the distal annular region. In general, the smaller the value of LDR, the better flexibility of the proximal annular region. Values of LDR are expect to be 0.25, 0.5%, 0.625% 0.75%, 1%, 1.25, 2%, 2.5%, 3%, 3.5%, 4, 4.5%, 5%, 10% the value of L. It is envisaged for most applications where the distal annular region will provide support LDR will be between 0.5 cm and 1 cm for a 40 cm elongate tubular member 1.

The internal diameter of the bend-resistive zone IDS is at the option of the user, in accordance with the size of cables or other elements that need to pass through the lumen. For surgical applications, a value of IDS between 1 mm to 8 mm, and 0.5 mm to 3 mm for endovascular application will cover most applications where fine control is necessary through a restrictive opening. Larger internal diameters are possible, for example, where mechanical structures are investigated and the size of the opening is not critical. The internal diameters of the proximal and distal bendable zones—IDP and IDD respectively—may be the same as the IDS. As mentioned previously, the diameter of the proximal bendable zones may gradually increase towards the proximal end in order to increase the bending couple i.e. leverage. According to one aspect of the invention, IDP may be 5%, 10%, 15%, 20%, 25%, 30%, 40%, 50%, 100%, 200%, 300%, 400%, 500%, 600%, 700%, 800%, 900%, 1000%, 2000% or more, greater than IDS or IDD at its widest point, or a value in the range between any two of the aforementioned values.

The external diameter of the bend-resistive zone ODS will be governed by the size of the internal diameter, and the opening available. For surgical application, a value of ODS between 1 mm to 8 mm will cover most applications where fine control is necessary through a restrictive opening. Larger external diameters are possible, for example, where mechanical structures are investigated and the size of the opening is not critical. The external diameters of the proximal and distal bendable zones—ODP and ODD respectively—may be the same as the ODS. As mentioned previously, the diameter of the proximal bendable zones may gradually increase towards the proximal end in order to improve flexibility. According to one aspect of the invention, ODP may be 5%, 10%, 15%, 20%, 25%, 30%, 40%, 50%, 100%, 200%, 300%, 400%, 500%, 600%, 700%, 800%, 900%, 1000%, 2000% greater than ODS or ODD at its widest point, or a value in the range between any two of the aforementioned values.

The thickness of the wall of the elongate tubular member 1 is generally the same throughout, i.e. values of TP (thickness of the wire in the proximal bendable zone), TS (thickness of the strip in the bend-resistive zone), and TD (thickness of the wire in the distal bendable zone), will be similar. The wall may have a substantially uniform thickness. For most applications, the inner diameter needs to be maximized compared with the external diameter. However, in certain application, the walls may be thick relative to the inner diameter, leaving a small inner lumen, for example, just for a control cable. The thickness of the wall may be 0.1 mm, 1 mm, 2 mm, 3 mm, 4 mm, 5 mm, or 6 mm, preferably between 0.1 to 0.6 mm, though the skilled person will appreciate it will vary according to the material properties. As mentioned earlier, the wall can be thinned in either or both bendable zones, typically by 1%, 2%, 3%, 4%, 5%, 6%, 7%, 8%, 9% or 10%.

The dimensions mentioned herein are provided strictly for guidance. The skilled person would appreciate that the dimensions of the elongate tubular member can be adapted within the teachings of the present invention and thus other dimensions are likewise feasible within the scope of the present invention.

Manufacture of the Tube

The transmission and bending properties of the elongate tubular member may be provided by the pattern of cuts e.g. longitudinal cuts in the bend-resistive zone 6 (transmission). Additional flexibility may be provided by cut-out apertures in the bendable zones 4, 5. A standard technique for the construction of a elongate tubular member of the present invention is laser cutting technology (FIG. 3A) which can produce the instrument in an automatic manner e.g. by computer numeric controlled (CNC) cutting. Adjustments to the cutting due to different lengths or diameters of tubular member 1 can be automatically computed and modified cutting regimes implement. Other methods may also be suitable, including water jet cutting, electrochemical etching, electrical discharge machining, diamond cutting, simple knife cutting, or any other suitable technique preferably followed by a suitable surface treatment, like etching or electro-polishing to deburr and or round off possible sharp edges.

As described elsewhere in the elongate tubular member may be formed from a flat sheet of material, appropriate cut, molded or stamped, that is bent cylindrically and joined at the mutual adjacent edges by virtue of interlocking circumferential joints in the distal 12 and proximal 11 annular regions to form a working elongate tubular member.

It is within the scope of the invention that each strip 8 of the elongate tubular member 1 is formed individually. Formation might be achieved using any number of techniques, for example, by a molding or stamping process. Molding processes are well known in the art; typically, a polymer in the liquid state is injected into a mold corresponding to the desired shape, in which the polymer hardens. The hardened product may be subjected to a suitable surface treatment, such as polishing to deburr and or round off possible sharp edges. Stamping techniques are well understood in the art; typically a cutting stamp, having an outline shape corresponding to the desired product shape is applied to a sheet of material such as polymer or metal. The product so formed may be curved by passing through rollers or by molding over a curved surface. The plurality of strips 8 so formed is used to assemble the elongate tubular member 1. It will be appreciated that the above techniques may be applied to form segments of the elongate tubular member 1. A segment comprises a strip 8, attached wires 9, 10 and a segment of the proximal 11 and distal 12 annular regions disposed with interlocking cut-outs or interconnections (e.g. dove-tail joints or the like) holding adjacent segments of the annular regions together circumferentially. In particular, the elongate tubular member 1 depicted in FIG. 14A may be formed in this manner.

Where the elongate tubular member 1 is formed from two or more different materials, for example, the bend-resistive zone 6 made from stainless steel and the bendable zones 4, 5 made from nitinol, said materials may be joined, for instance, by welding or gluing together intact tubes prior to cutting, and then cutting the compound tube so formed. Alternatively, separate tubes formed from the different materials may be cut according to the invention that are later joined using joints created by the cutting process as seen, for example, FIG. 16B. Alternatively, separate elements of the elongate tubular member (e.g. strips 8, wires 9, 10, proximal and distal annular regions 11, 12) may be formed separately, and joined, for example, by welding, gluing or soldering.

Outer Sheath

An outer sheath 20 (FIGS. 2A and B, FIG. 7) may be present in a steerable tube of the invention, which outer sheath 20 at least partly covers the outside surface of the hollow elongate tubular member 1. Preferably, the outer sheath 20 covers at least the bend-resistive zones 6 and the bendable zones 4, 5. The outer sheath 20 protects the hollow elongate tubular member 1 from dirt and obstruction while permitting translational movements of the strips 8, 8' and wires 9, 9', 10, 10' within. In this regard, the outer surfaces of the strips 8, 8' and wires 9, 9', 10, 10' may be coated with a lubricating substance, such a Teflon or silicone. In addition, the surfaces (e.g. outer and/or inner) of the outer sheath 20 may also be coated with a lubricating substance, such a Teflon or silicone. The outer sheath may play a constraining role to prevent the strips 8, 8' and wires 9, 9', 10, 10' from bending outwards. Therefore, the outer sheath will have the necessary tensile properties, showing no or little elastic behaviour in order to constrain radial forces of the strips 8, 8' and wires 9, 9', 10, 10'. The outer sheath 20 may be liquid or gas impermeable. The outer sheath 20 is preferably thin-walled, and constructed to exhibit flexibility in the bendable zones 4, 5. It is preferably cylindrical.

Figure 7:
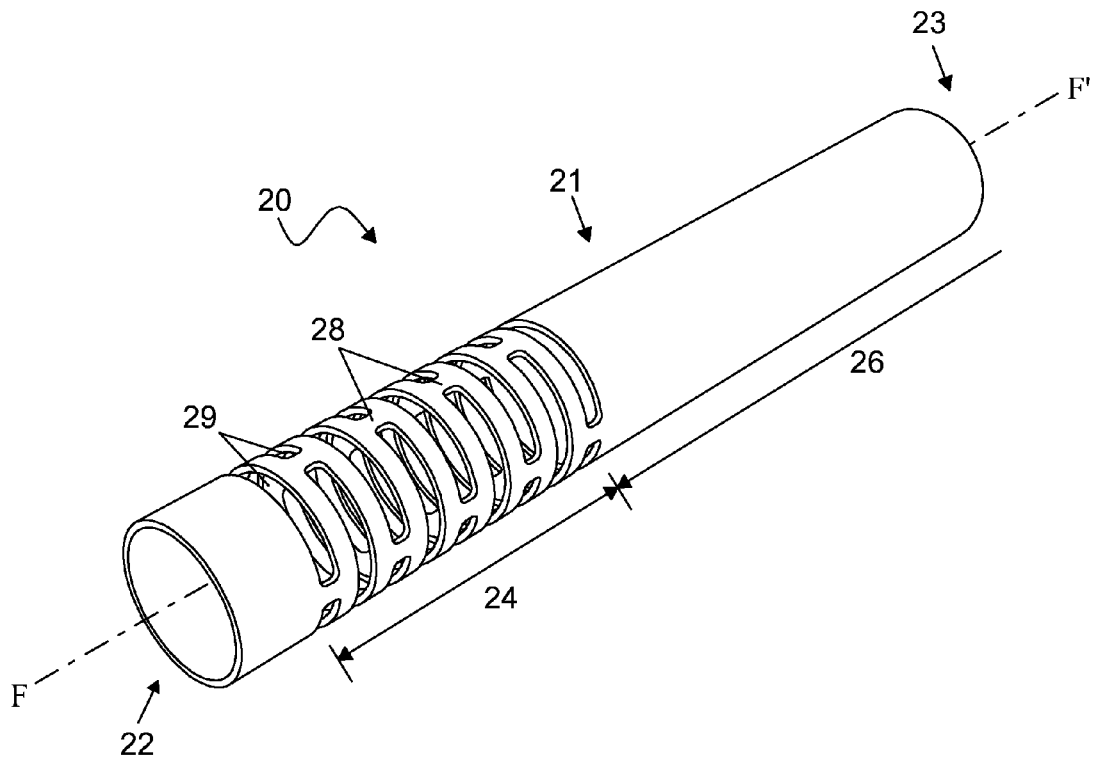
FIG. 7 depicts a perspective view of an outer sheath.

In a preferred aspect of the invention, and with reference to FIG. 7 the outer sheath 20 is made of a hollow tube 21 having a proximal end 22, distal end 23, a wall surface disposed between said proximal 22 and distal end 23, the wall having a substantially uniform thickness, a flex-resistive region 26 flanked by proximal 24 and distal 25 flexible regions, whereby the internal diameter of the hollow tube 21 is greater than the external diameter of the elongate tubular member 1. The hollow tube 21 is preferably placed over the tubular member 1 and co-axially aligned therewith so that the flex-resistive region 26 covers the bend-resistive zone 6, the proximal 24 and distal flexible regions cover the proximal 4 and distal 5 bendable zones of the elongate tubular member 1 respectively.

The wall of the hollow tube 21 in the flex-resistive region 26 is essentially intact, preferably being devoid of slits or apertures. The flex-resistive region 26 is less flexible than the flexible regions 24 of the outer sheath. The wall of the hollow tube 21 in the proximal flexible region 24 and the distal flexible region may comprise a structure that is a plurality of linkages 28 separated by strain-relief apertures 29, which linkages 28 and apertures 29 allow the second tubular member to flex. Two or more separate series of such apertures 29 may be formed adjacent one another on opposite or different sides as shown in FIG. 7 of the tubular body to permit deflection or bending of the tubular body in multiple directions about its longitudinal axis (F-F'). Other known techniques that make rigid tubes more flexible are the use of spiral cuts, hinges cuts, dove-tail cuts, and heart-like cuts. The apertures and patterns can be cut using the methods mentioned herein, in particular laser cutting technology. To better control the bending radius, for instance less bending in the distal portion of the proximal bending zone, the apertures (or linkages) may have different sizes. The hollow tube 21 can be made from any biocompatible material which provides the requisite elastic and flexural properties. Suitable materials include stainless steel, cobalt-chromium, shape memory alloy such as Nitinol®, plastic, polymer, composites or other curable material.

FIG. 7 depicts a perspective view of an instance of an outer sheath 20. Shown is the wall of the sheath 21 in the flex-resistive region 26 devoid of apertures. The essentially continual wall structure reduces the flexibility of the flex-resistive region 26.

It is within the scope of the invention, that the outer sheath 20 is formed from a tube that has inherent flexible properties, for example being made from material such as PTFE, polypropylene, or other silicone or rubberised polymeric substances which exhibits flexibility in the proximal bendable zone 4 and the distal bendable zone 5 when the outer sheath co-axially covers the elongate tubular member 1. The region covering the bend resistive zone 6 may be reinforced with to resist radial expansion or increase torsional stiffness, for example, using braiding. To prevent penetration of substances through the strain-relief apertures, an additional liquid impermeable cover (PTFE, silicone, heat shrink wrapper) may be utilised.

According to one aspect of the invention, the outer sheath 20 incorporates a braking mechanism, configured, when activated to prevent slidable movements by the strips 8, 8' of the elongate tubular member 1. When the brake is applied, the position of the distal bendable zone 5 is fixed; i.e. it becomes resistive to force applied thereto. The brake may take any form, for example, a compressible annular ring having an inner diameter that varies according to the degree of compression. The inner circumference of the ring applies pressure to the strips 8, 8' of the elongate tubular member 1 when the ring is compressed along its central axis.

As already mentioned above, the outer sheath can be omitted by observing a more complex cutting pattern; the strips 8, 8' are envisaged which are held together (interlocked) using interconnections (FIG. 8C), non-longitudinal slits (FIG. 8A), non-radial slits (FIG. 8B) or longitudinal spiral cuts. In this constellation, the inner and outer coverings may be, but not necessarily, omitted. In this way, issues of sterilization, concerning access of steam or plasma to all areas and tubes, can be circumvented.

Inner Lining

An inner lining 50 (FIGS. 2A and B) may be present that at least partly lines the lumen 15 of the hollow elongate tubular member 1. The inner lining 50 protects the inside hollow elongate tubular member 1 from dirt and obstruction while permitting translational movements of the strips 8, 8' and wires 9, 9', 10, 10' outside. In this regard, the inner surfaces of the strips 8, 8' and wires 9, 9', 10, 10' may be coated with a lubricating substance, such a Teflon or silicone. In addition, the surfaces (e.g. outer and/or inner) of the inner lining 50 may also be coated with a lubricating substance, such a Teflon or silicone. The inner lining may play a constraining role to prevent the strips 8, 8' and wires 9, 9', 10, 10' from bending inwards. Therefore, the inner lining will have the necessary compression properties, showing no or little elastic behaviour in order to constrain radial forces of the strips 8, 8' and wires 9, 9', 10, 10'. The inner lining 50 may be liquid or gas impermeable. The inner lining 50 is preferably thin-walled, and constructed to exhibit flexibility in the bendable zones 4, 5. It is preferably cylindrical.

Preferably, the inner lining 50 is formed from a tube that has inherent flexible properties, employing a material such as PTFE, polypropylene, or other silicone or rubberised polymeric substances. The inner lining 50 may be formed from an inherently inflexible tube, made flexible by the addition of apertures cut from the tube walls and as described elsewhere herein. Preferably, the hollow tube is flexible over its whole length.

The use of an inner lining 50 is not essential. The lumen 15 of the hollow elongate tubular member 1 can be obturated for example with a laser fiber, control cable for grasping forceps or scissors, aspiration catheter, bundle of glass fibers, power or data cables, a flexible rod with a lumen for electrical wires.

Figure 2:
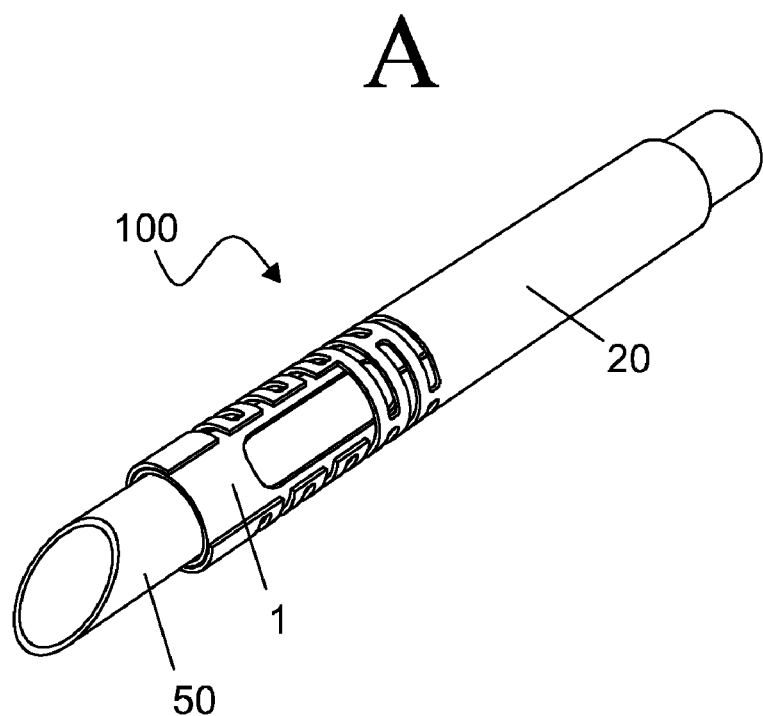
FIG. 2A shows cut away section device of the present invention comprising an elongate tubular member 1, disposed with both optional outer sheath 20 and inner tube 50. The outer sheath and inner tube, explained below as not being essential, are shown to facilitate comparison with the prior art.
FIG. 2B shows axial view section device of the present invention, together with indications of outer (OD) and inner (ID) tube diameters. A favorable comparison with the dimensions of devices known in the art is apparent.
Figure 2:
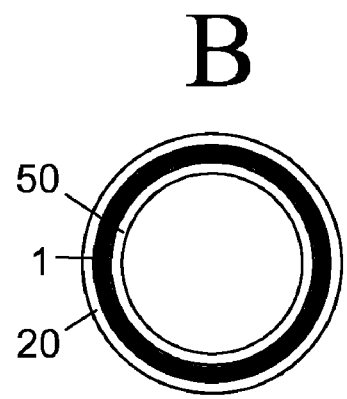

According to one aspect of the invention, the inner lining 50 is made of a hollow tube having a proximal end, distal end, a wall surface disposed between said proximal and distal end, the wall having a substantially uniform thickness, a flex-resistive zone flanked by proximal and distal flexible region, whereby the external diameter of the hollow tube is less than the internal diameter of the tubular member 1. The hollow tube is preferably placed within the tubular member 1 and co-axially aligned therewith so that the flex-resistive region covers the bend-resistive zone, the proximal and distal bendable zones cover the proximal 4 and distal 5 and flexible regions respectively. FIG. 2B depicts an inner lining 50 within the proximal bendable zone 4, having walls containing apertures and linkages, similar to the hollow tube 21 that forms the outer sheath 20. The embodiments above and which describe FIG. 5 of the outer sheath 20 may be readily adapted to prepare an inner lining with the above mentioned properties.

Figure 13:
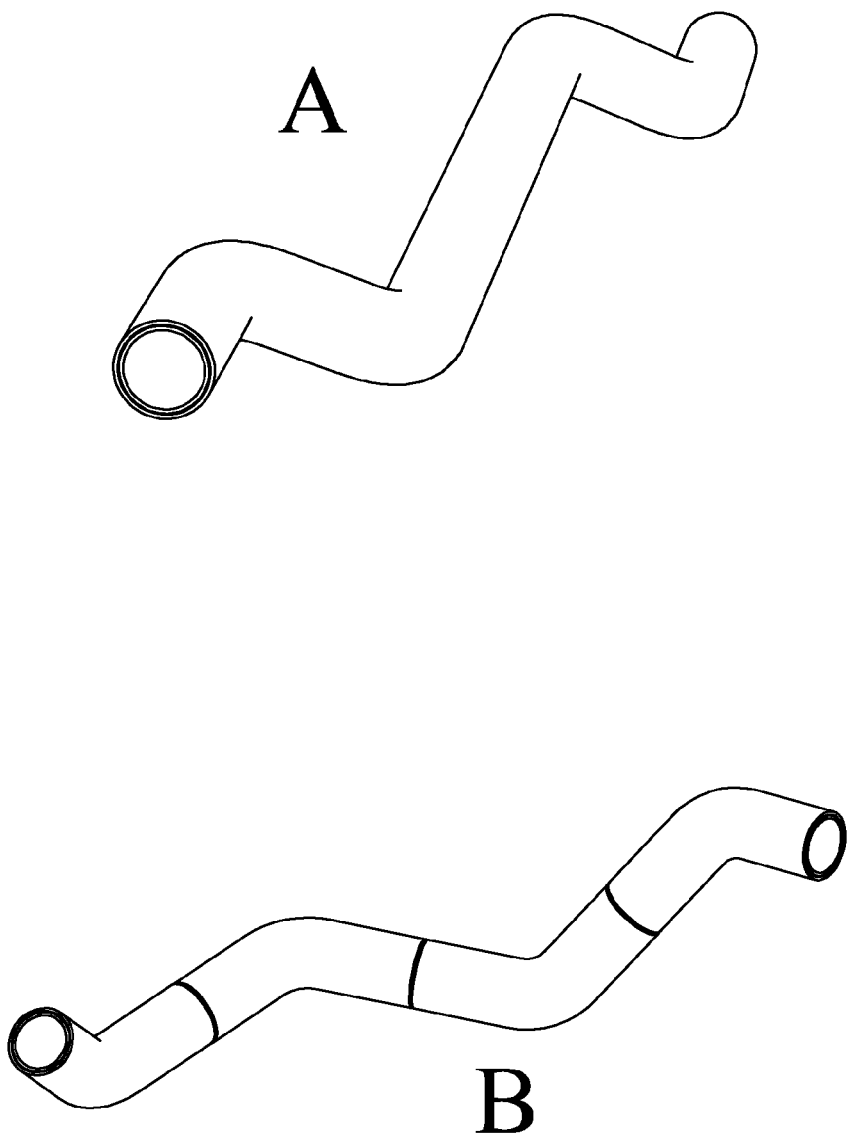
FIG. 13A illustrates a perspective view of coaxial steering tubes
FIG. 13B depicts a sequence of tandemly arranged steerable tubes (motorized), forming a snake-like articulated tube having several degrees of freedom of movement.

Additionally coaxial steering tubes can allow indifferent flexion on different parts of the complete tube FIG. 13A. This could allow surgeons to go through one incision with two or more instruments. After entering the abdomen a first joint brings the instrument lateral while a second allows coming back medially towards the operative field. This concept allows performing the operation through one incision while maintaining an on-obstructed view on the operative field.

Adaptations

Figure 15:
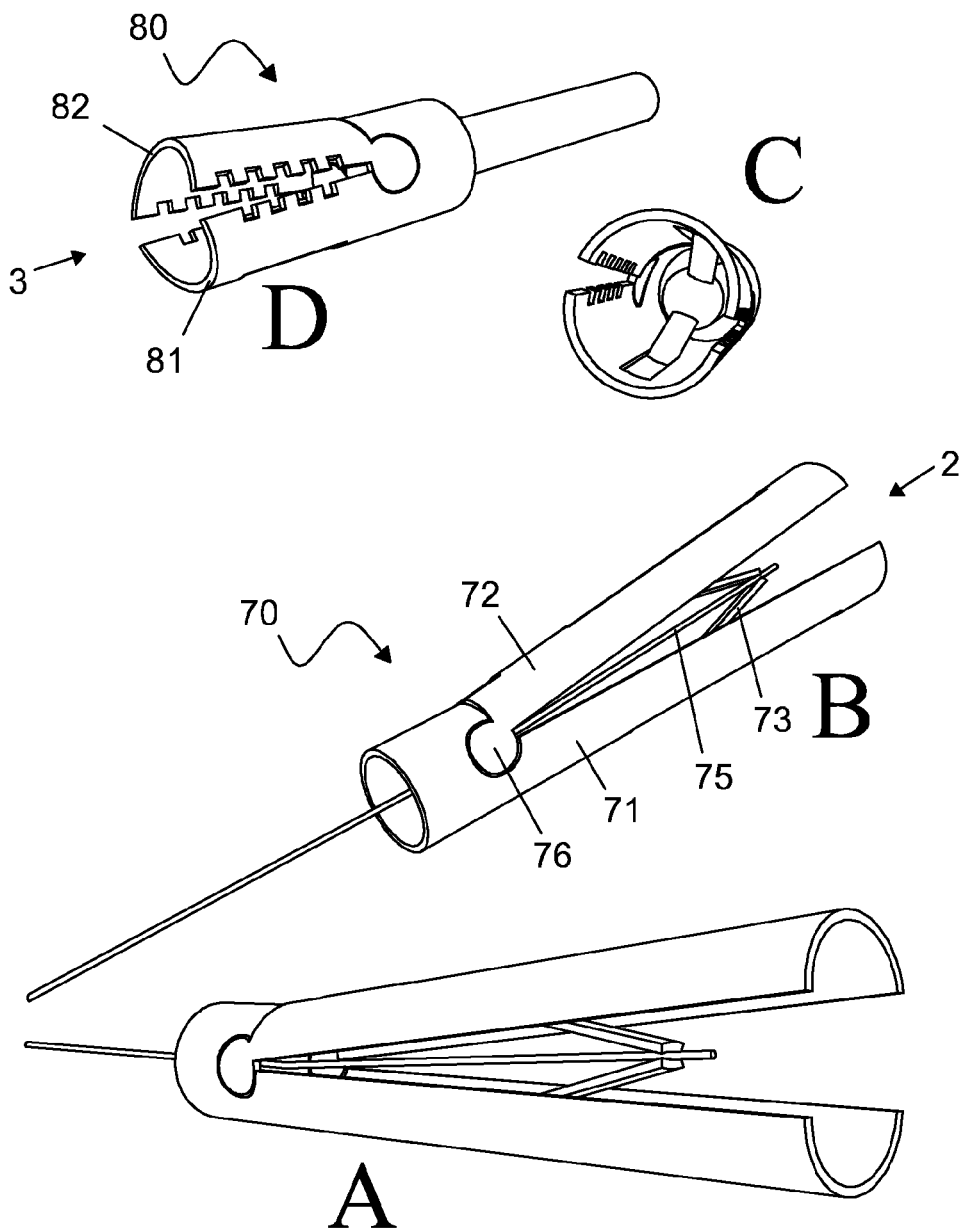
FIGS. 15A to 15D provide perspectives view of a steerable tube adapted with a gripper (FIGS. 15A and B) and forceps (FIGS. 15C and D).

As mentioned earlier, the proximal or distal ends of the instrument may be adapted with particular tools or components which may be attached to the tubular member, and/or to the optional outer sheath and/or to the optional inner lining. According to one example, the proximal end 2 may be adapted with a handgripper 70 which controls a set of forceps 80 at the distal end 3, which forceps 80 are controlled by a control cable 75 passing through the lumen, connected to the handgripper 70 (FIGS. 15A to 15D). The handgripper 70 may be formed from an essentially solid-walled thin tube, cut according to the techniques described herein. Such handgripper is shown in FIGS. 15A and 15B. The two handles 71, 72 of the gripper 70 are formed by a pair of longitudinal cuts, and one hinge handle 72 is created by a circumferential cut which creates two revolute joints 76 at the corners of the one hinge handle 72. Supporting struts 73 for the control cable 75 may be cut from the handles 71, 72. Alternatively, instead of supporting struts an additional laser cut ring-like structure that becomes oval when compressing the handles may be employed. In this way, hinged movement by the handle 72 is converted to a linear movement by the wire 75.

Similarly, the forceps 80 may be formed from an essentially solid-walled thin tube, cut according to the techniques describe herein. Such forceps 80 is shown in FIGS. 15C and 15D. The two jaws 81, 82 of the forceps 80 are formed by a pair of longitudinal cuts, and one hinge handle 72 is created by a circumferential cut which creates two revolute joints 76 at the corners of the one hinge handle 72. A supporting strut 83 for the control cable 75 may be cut from the two jaws 81, 82. In this way, a linear movement by the control cable 75 is converted to a hinged movement by the jaw 82.

According to one embodiment of the invention, the strips 8, 8' of the hollow elongate tubular member 1 are made from one material, while the wires 9, 9' are made from another material. The wires and strips 8, 8' are joined by interconnecting joints (FIG. 16A). Such hybrid structure might be of use to reduce the costs when expensive material are employed such as Nitinol; in such case, Nitinol may be used to form the wires 9, 9' and annular regions 11, 12, while a cheaper alloys used to form the strips 8. Alternatively the wire could be replaced by small Nitinol rods inserted in the annular region and strips (FIG. 16B).

For difficult-to-see and/or hard-to-reach places, the distal end 3 may advantageously by provided with an endoscopic camera or lens, which may be implemented by fiber scope or chip-on-a-stick.

According to one aspect of the invention, the steerable tube 100 further comprises a cutting tool at the distal end 3. The cutting tool can be any, including but not limited to scissors, knife, drill, mill, grinder, saw, or knibbler.

According to another aspect of the invention, the steerable tube 100 further comprises a sensor at the distal end 3. The sensor is preferably electronic, and concerts the detected phenomenon into electrical signals. The sensor can be any, including, but not limited to temperature, moisture, light (wavelength and/or intensity), gas, radioactivity, acoustic, and pressure.

According to one aspect of the invention, the steerable tube 100 further comprising one or more electrodes at the distal end 3. The electrode can be any, including, but not limited to stimulation, recording, coagulation, reference.

Another embodiment of the invention is an endoscope disposed with a plurality of lumens, whereby at least one lumen (for example, 1, 2, 3 or more) is provided with a steerable tube of the present invention. It is noted that the narrow profile of the steerable tubes allows the construction of an endoscope of standard diameter (e.g. 6.2 mm) comprising two steerable tubes, one in each lumen. Exceptionally, the presence of two steerable tubes permits co-operation at the tip, exemplified with one tube being disposed with a remote-controlled jaw to grasp an object and another tube disposed with a remote-controlled cutter, to sever the object. This level of control and co-operation between instruments has never before been achieved through narrow tube endoscopes. Further, the wide internal diameter of the steerable tube facilitates its role in aspiration such that excised tissue can be removed through the steerable tube without blockage. It is envisaged that, particularly in bodily-invasive procedures, the invention permits safer and more rapid manipulations while reducing the risk of infections.

Steering Guide

Figure 17:
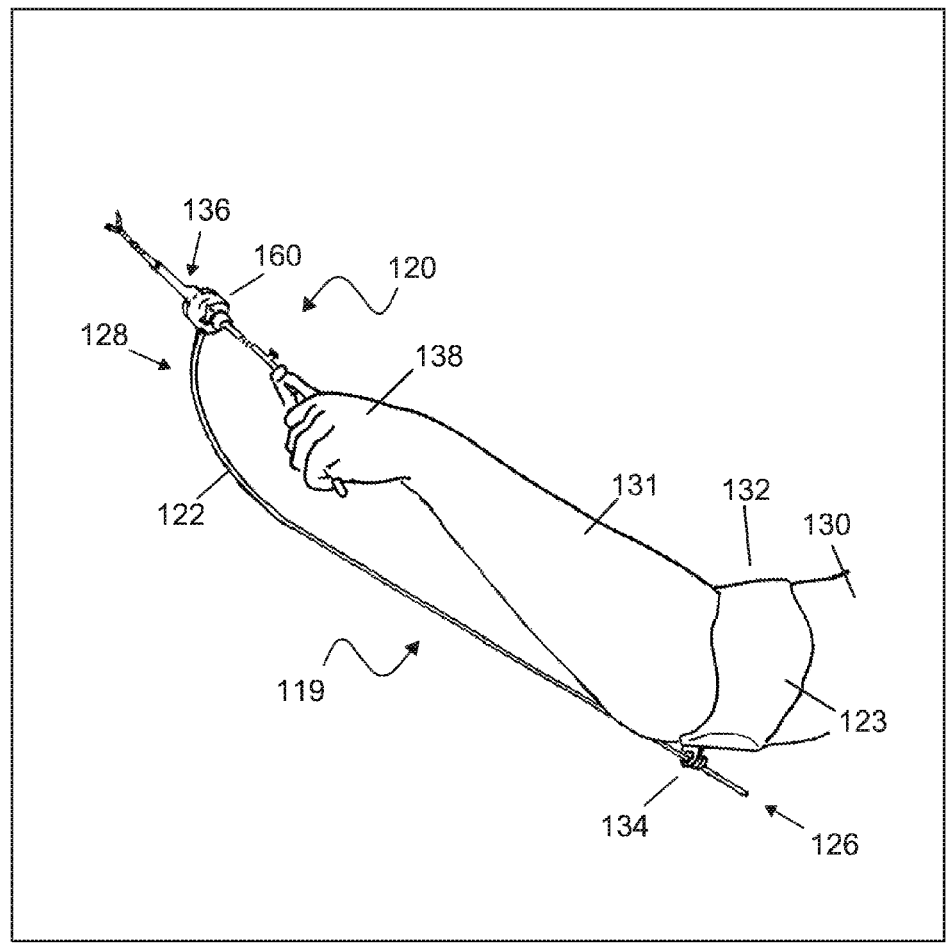
FIG. 17 shows a schematic view of a steering guide for supporting and pivotally moving an invasive medical instrument having a longitudinal axis, within a bodily cavity.

Another embodiment of the invention is a steering guide 119, exemplified in FIG. 17, configured for attachment to a part of the bodily arm of the user and which supports, through an attached endoport device 160 (described further below), an invasive medical instrument 120 disposed with a longitudinal axis, including, but not necessarily limited to the steerable tube 100 of the present invention, permitting pivotal movement of the instrument 120, said pivotal movement actuated by said part of the arm. The pivotal movement referred to herein is the movement within a conical space around the point of a cone centered on a fulcrum point. Thus, the pivotal movement of the endoport device 160 attached to the steering guide is around a fulcrum point 136. The fulcrum point 136 of the endoport device 160 coincides with a point along the device body where it rests in the incision. The steering device positions the proximal end of the instrument 120 within reach of the user's hand 138 which can access and operate controls thereon, independent of adjusting the pivotal position of the instrument, which is performed by the arm. The user's wrist joint effectively isolates movements by the hand 138 from movements of the arm part. The steering guide 119 takes advantage of the isolated movement to operate any proximally-situated controls of the medical instrument simultaneous with adjusting its position in the available working space.

The steering guide 119 may comprise an elongated longitudinal member 122 having a proximal 126 and distal 128 end, the proximal end 126 disposed with a brace 123 for attachment to a part of a bodily arm, and the distal end 128 disposed with an endoport device 160, configured for attachment to the medical instrument 120.

The elongate longitudinal member 122 is essentially rigid, and at least spans the length between the brace 123 and a point distal to (beyond) the hand 138 of the user. It is preferably made from a light weight material such as aluminum, titanium, polymer (e.g. polycarbonate), or composite. It may be formed from a solid rod, hollowed rod, or from a rod with transverse openings. The material used to form the elongate longitudinal member 122 may not inherently posses the requisite rigidity in the rod form, in which case the structure may be strengthened with one or more cross supports. The elongate longitudinal member 122 may be straight at least in part. The distal end 126 may be shaped (e.g. curved) to create a volume that accommodates a range of movement by the hand 138. The distal end 126 may be further shaped (e.g. curved) to bring the endoport device 160, in particular the passage therethrough, in co-axial alignment with the longitudinal axis of the lower arm 128.

The brace 123 attaches the elongated longitudinal member 122 to a part of the bodily arm of the user. The brace 123 may be adapted for attachment to any part of the arm, for instance, the upper arm 130, lower arm 131 or elbow 132. The brace 123 may be attached to the proximal end 126 of the elongated longitudinal member 122 using a fixture 134 that allows slidable movement of the elongated longitudinal member 122 relative to the brace 123. The fixture 134 may further be configured to limit or allow pivotal movement of the elongated longitudinal member 122 relative to the brace 123. The fixture 134 exemplified in FIG. 17 comprises a protruding rigid eyelet through which the elongate longitudinal member 122 passes, and can pivot and slide relative to the eyelet. The brace 123 may be configured to orientate the longitudinal member 122 essentially parallel to the lower arm 131. The brace 123 may be configured to position the endoport device 160 at a point distal to (beyond) the hand 138 of the user. Movements of the arm, e.g. the upper arm 130, lower arm 128 or elbow 132 are directly transmitted along the elongated longitudinal member 122 to the endoport device 160 which they are realised as pivotal movements.

The brace 123 may be formed from a cylindrical ring, with a central passage in which the arm part lies. It is preferably formed from an inelastic cloth cuff configured to wrap around the arm part, and disposed with a securing means such as one or more Velcro® strips.

The endoport device 160 is attached to the distal end 128 of the elongated longitudinal member 122. The endoport device 160 is configured to couple with the longitudinal axis of the medical instrument 120. The endoport device 160 may permit slidable and rotational movement of the medical instrument relative thereto, which movements are lockable. Typically the endoport device 160 comprises a cylindrical passage in which the instrument 120 rests, and optionally a locking mechanism that holds the instrument 120 in fixed position with respect to the endoport device 160. The locking mechanism may comprise a nut or pin, that frictionally contacts and applies locking pressure to the body of the instrument. The central axis of the cylindrical passage of the endoport device 160 is preferably substantially co-axially aligned with the longitudinal axis of the lower arm. The endoport device 160 may attach to the elongated longitudinal member 122 with an adjustable joint configured to lockably adjust the orientation of the central axis of the cylindrical passage relative to the longitudinal axis of the lower arm. The joint may permit rotational movement by the endoport device 160 in two or three dimensions.

The elongated longitudinal member 122 may be rigidly attached to an open kinematic chain comprising a plurality (e.g. 2, 3, 4, 5, 6 or more) of tandemly arranged, rigid links, connected by lockable joints (e.g. revolute and/or ball and socket), which kinematic chain permits movement of the elongated longitudinal member 122 when the joints are not locked, and which prevents movement by the elongated longitudinal member 122 when the joints are locked. The open kinematic chain typically has a base link, rigidly attached at one end to the operating table, and an effector link attached to the elongated longitudinal member 122. One or more links may be disposed between the base and effector links. It will be understood that, in accordance with kinematic principles, the more joints employed, the more degrees of freedom of movement permitted by the longitudinal member 122 attached to the effector link. Typically the total number of joints is 3, 4, 5, 6 or 7 or more. A 6 joint open kinematic chain provides 6 degrees of freedom in its workspace. The locking mechanism of the revolute joints can be any, including a mechanical, electromagnetic, pneumatic or hydraulic brake, preferably actuated by a foot pedal or lever.

The steering guide is suitable for use with any medical instrument that would benefit from setting its pivotal orientation, such as the steerable tube of the invention, any steerable tube, or a laparoscope. In general the medical instrument has a longitudinal axis, and a body that is capable of being held by the endoport device 160.

The pivotal movements of the medical instrument 120 are actuated by a part of the human arm, for instance, the upper arm 130, lower arm 131 or elbow 132, leaving the hand free to operate the instrument, for instance, levers, buttons, controllers, disposed at the instrument's proximal end. When the instrument is a steerable tube 100 of the present invention, the hand is able to operate the controller at the proximal end so changing the position of the tube distal end, in addition to operating any handles e.g. for a distal cutter or gripper, without disturbing the pivotal position of the instrument which is controlled by a separate part of the body i.e. the arm, optionally locked by a lockable kinematic chain.

Lockable Articulated Arm

Another embodiment of the invention is a lockable articulated arm comprising a plurality (e.g. 2, 3, 4, 5, 6 or more) of tandemly arranged, rigid links connected by lockable joints, having at one end a base link configured for rigid attachment to an operating table, and at the other end, an effector link connected to a lockable ball and socket joint, the ball and socket joint configured for coupling to an endoport device, through which a medical instrument disposed with a longitudinal axis, including, but not necessarily limited to, the steerable tube of the present invention is disposed, which lockable ball joint is further configured to pivot the endoport device relative to the effector link. The lockable articulated arm allows the user to orient the effector link within a working volume and to set the desired position. Having set the desired position in three-dimensional space, the medical instrument disposed on the effector link may be independently pivoted around the ball and socket joint, and the desired pivotal position also locked.

Figure 18:
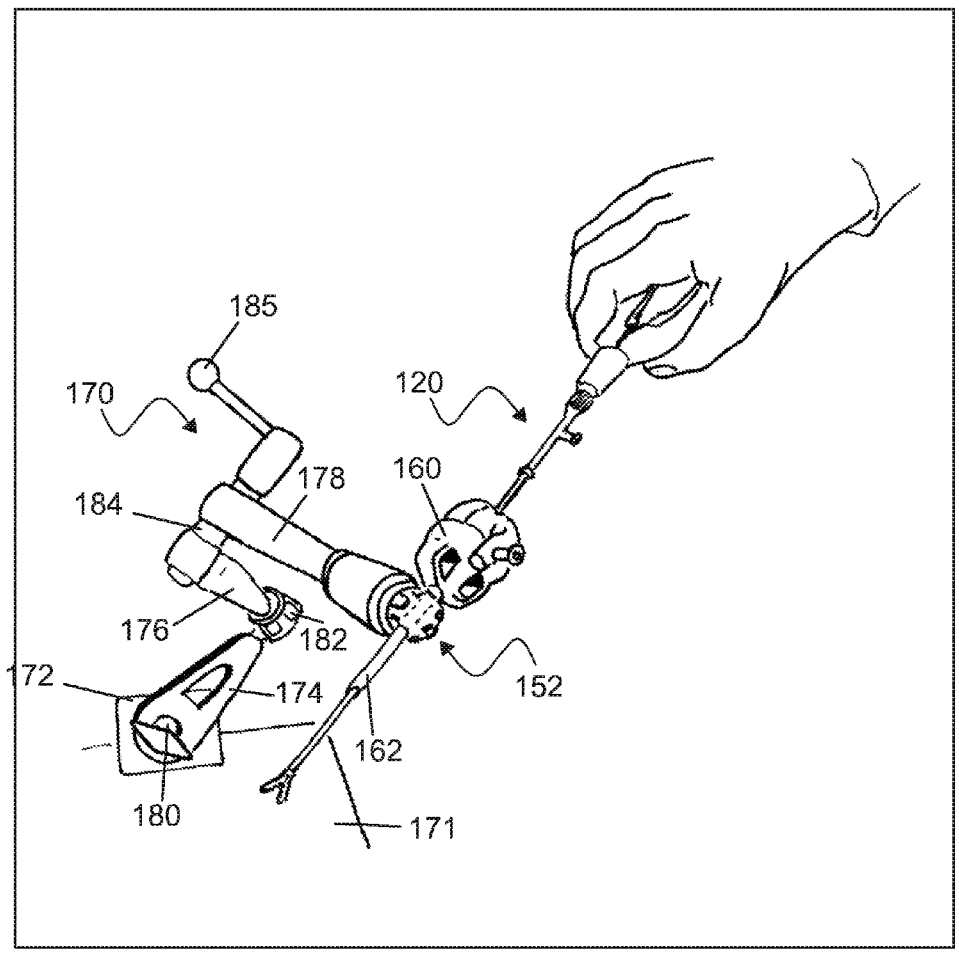
FIG. 18 shows a schematic view of a lockable articulated arm of the invention.

According to one aspect of the invention, the lockable articulated arm, as shown in FIG. 18, comprising a plurality of tandemly arranged, rigid links 172, 174, 176, 178 connected by lockable joints 180, 182, 184, which arm 170 permits movement of the links 172, 174, 176, 178 when the joints 180, 182, 184 are not locked, and which prevent movement by the links 172, 174, 176, 178 when the joints 180, 182, 184 are locked. The articulated arm 170 typically has a base link 172, rigidly attached at one end to the operating table 171, and an effector link 178 connected at one end to a ball and socket joint 152 to which an endoport device 160 attaches, and through which an invasive medical instrument 120 disposed with a longitudinal axis, including, but not necessarily limited to the steerable tube 100 of the present invention is disposed. One or more links 174, 176, may be disposed between the base 172 and effector 178 links. It will be understood that the more joints employed in the arm, the greater the degree of freedom of movement i.e. working space permitted by the terminal end of the effector link 178, and thus by the medical instrument 120 attached thereto. Typically the total number of joints is 3, 4, 5, 6 or 7 or more.

One pair of links is preferably connected by one joint. It will also be appreciated that the type of joints 180, 182, 184 employed between the links 172, 174, 176, 178, whether they be revolute, ball and socket, or a mixture, also influences the volume of the working space of the terminal end of the effector link 178. In FIG. 18, the first joint between the base link 172 and the first link 174 is revolute; the second joint 182 between the first link 174 and second link 176 is a ball and socket joint; the third joint 184 between the second link 176 and third link 178 is revolute.

The locking mechanism of the joints 180, 182, 184 can be any, including a manual mechanical mechanism actuated by a lever 185 as shown in FIG. 18, or electromagnetic, pneumatic or hydraulic brake, preferably actuated by a foot pedal. Preferably the joints lock simultaneously.

The ball-joint port 152 is also lockable (FIG. 19), meaning that the pivotal position of the endoport device 160 can be set and locked at a position within the range of possible movement of the ball joint. The locking mechanism can be any, including, for example, a pin, screw, or collar that frictionally contacts the ball 154 when advanced there towards, or a contractable socket 156.

As described earlier, the effector link 178 is attached to one part of a ball and socket joint (e.g. the socket), while the other part of the joint (e.g. the ball) attaches to the endoport device. According to the embodiment depicted in FIG. 19, the ball 154, having a spherical shape, is provided with a diametric bore 158 passing completely through the ball, adapted to support the endoport device 160. The bore 158 may be configured to permit no or limited slidable or axial-rotational movement by the endoport device 160 relative to the ball 154. The ball 154 may incorporate a locking mechanism allowing slidable movement by the endoport device 160 in an unlocked mode, and substantially no slidable or axial-rotational movement by the instrument relative to the ball 152 in a locked mode.

Figure 19:
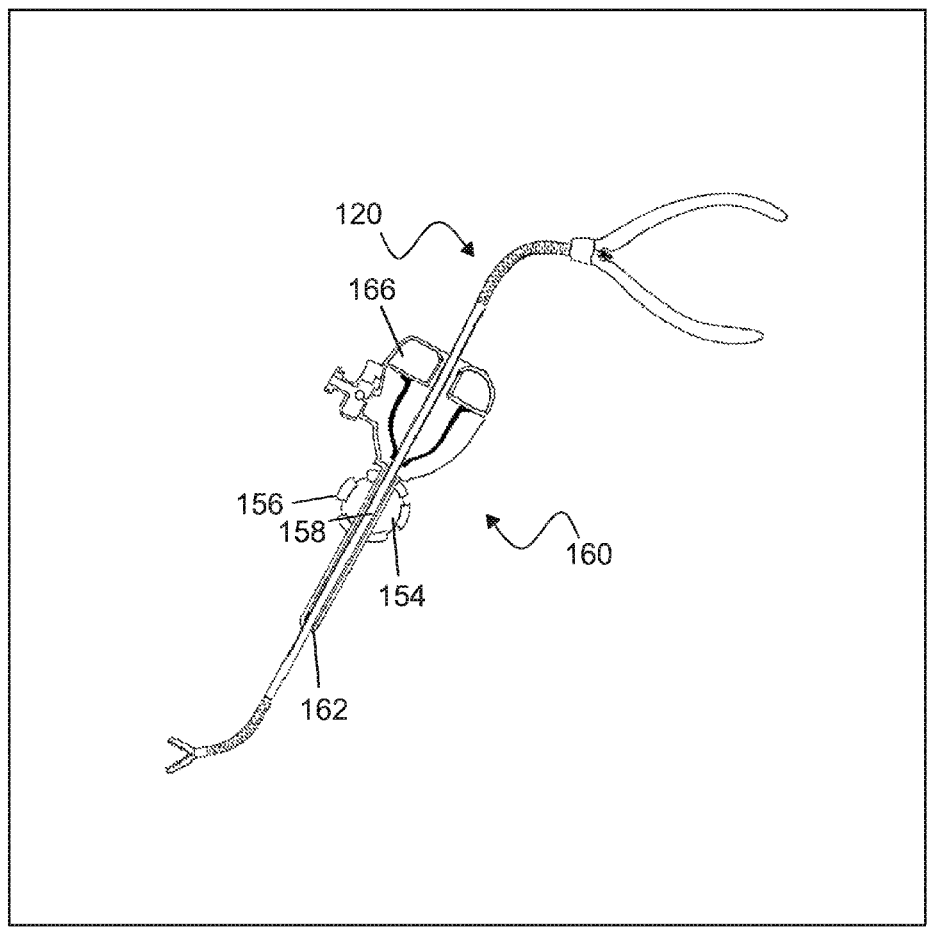
FIG. 19 shows a cross-sectional view of the ball and socket joint and endoport that forms part of the lockable articulated arm.

The endoport device 160 used in both the steering guide 119 and lockable articulated arm 170 is known in the surgical field. For guidance, a brief description follows. The endoport device 160 comprises a hollow tubular member 162 configured for insertion through an incision in a subject (e.g. a patient), open at one end, and is attached at the other end to a head section 166 comprising a fitting 164 for a source of pressurised gas such as carbon dioxide. The fitting 164 may be a Luer fitting, preferably provided with a screw thread. Gas passing through the fitting 164 is directed to the hollow tubular member 162, thereby permitting inflation of the cavity being surgically accessed when the device is in situ. The hollow tubular member 162 may be disposed with one or more side ports (not shown) for gaseous outlet. The head section 163 further comprises a linear passage in coaxial alignment with the central axis of the hollow tubular member 162 which passage is also in fluidic connection with the hollow of the tubular member 162. The combined cylindrical passage so formed, spanning the head and tubular member is suitable for receiving an invasive medical instrument 120 disposed with a longitudinal axis, including, but not necessarily limited to the steerable tube 100 of the present invention. When used in conjunction with the lockable articulated arm 170 of the invention, part of the hollow tubular member 162 of the endoport device 160 attaches to the ball and socket 152. As shown in FIGS. 18 and 19, the hollow tubular member 162 passes trough the bore 158 of the ball 153, and contacts the head 166.

The lockable articulated arm 170 is suitable for use with any medical instrument that would benefit from setting a spatial and pivotal orientation, such as the steerable tube of the invention, any steerable tube, or a laparoscope. In general the medical instrument has a longitudinal axis and a body that capable of being held within the bore 158 of the ball 154.

The particular combination of parts described and illustrated herein is intended to represent only one embodiment of the invention, and is not intended to serve as limitations against alternative devices within the spirit and scope of the invention.

The invention claimed is:

1. A steerable tube, comprising a hollow elongate tubular member having a proximal end, distal end, a wall surface disposed between said proximal and distal end, a bend-resistive zone flanked by a proximal bendable zone that forms a controller and a distal bendable zone that moves responsive to movements of the controller, whereby
   the wall of the tubular member in the bend-resistive zone comprises a structure that is a plurality of longitudinal slits, forming a plurality of longitudinal strips,
   the wall of the tubular member in the proximal bendable zone and the distal bendable zone comprises a structure that is a plurality of longitudinal wires,
   at least one strip is in connection with a wire in the proximal bendable zone and a wire in the distal bendable zone, such that translation by said wire in the controller is transmitted via the strip to said wire in the distal bendable zone,
   a proximal annular region of the tubular member is proximal to the proximal bendable zone, to which the proximal wires are rigidly attached, and
   a distal annular region of the tubular member is distal to the distal bendable zone to which the distal wires are rigidly attached.

2. Steerable tube according to claim 1, wherein the proximal annular region and distal annular region are circumferentially intact.

3. Steerable tube according any claim 1, wherein one or more of the longitudinal strips is aligned or inclined to a longitudinal axis of the hollow elongate tubular member.

4. Steerable tube according to claim 1, wherein one or more of the longitudinal strips comprises interconnections, non-radial slits or spiral cuts to hold the strips together.

5. Steerable tube according to claim 1, wherein a wire in a bendable zone is of the same width or more narrow than a strip in the bend-resistive zone.

6. Steerable tube according to claim 1, wherein the narrowest circumferential width of a wire, is between 0%, and 90% less than the narrowest circumferential width of a strip.

7. Steerable tube according to claim 1, wherein one or more of the wires is at least partly linear.

8. Steerable tube according to claim 1, wherein the proximal bendable zone and/or distal bendable zone is substantially formed from a material different to that of the bend-resistive zone.

9. Steerable tube according to claim 1, further comprising an outer sheath, at least partly covering the outside surface of the hollow elongate tubular member while permitting translational movements of the strips and wires within.

10. Steerable tube according claim 9, wherein the outer sheath, is flexible in the region covering at least the bendable zones.

11. Steerable tube according claim 9, wherein the outer sheath, is less flexible in the region covering the bend-resistive zone compared with in the region covering at least the bendable zones.

12. Steerable tube according to claim 1, further comprising an inner lining that at least partly lines the lumen of the hollow elongate tubular member while permitting translational movements of the strips and wires outside.

13. Steerable tube according to claim 1, having one or more spacers configured to maintain distance between the wires.

14. Steerable tube according to claim 1, further comprising a handgripper at the proximal end, configured to control a set of forceps at the distal end.

15. Steerable tube according to claim 1, further comprising an endoscopic camera or lens at the distal end.

16. Steerable tube according to claim 1, whereby the zones are formed from a substantially solid tube wall of the hollow tubular member during manufacture, and the bendable zones are formed by removing material from said substantially solid tube wall.

17. Steerable tube according to claim 1, whereby the proximal annular region and/or distal annular region are formed from one or more interlocking elements configured to interlock around the circumference of the respective annular region.

18. Steerable tube according to claim 1, whereby the wire in the proximal bendable zone and/or the wire in the distal bendable zone is connected to the at least one strip by welding, gluing, soldering or by interlocking.

19. Steerable tube according to claim 1, whereby the thickness of the wire in the proximal bendable zone in its thinnest region and/or the wire in the distal bendable zone is less than that of the at least one connecting strip in its thinnest region.

20. Steerable tube according to claim 1, whereby the wire in the proximal bendable zone and/or the wire in the distal bendable zone is made from a more flexible material than use in the at least one connecting strip.

21. Steerable tube according to claim 1, wherein the elongate tubular member comprises a side port formed from an aperture between two adjacent strips.

22. Steerable tube according to claim 1, wherein the elongate tubular member incorporates a limit stop mechanism that limits the extent of relative slidable movement between two strips.

23. Steerable tube according to claim 9 or claim 12, whereby elongate tubular member, and one of the outer sheath, or inner lining are coaxially rotatable elements, further comprises a rotation limiting mechanism formed from a radial protrusion present in any one coaxially rotatable element, in longitudinal slidable connection with a reciprocating slot in another coaxially rotatable element of the steerable tube configured to reduce or prevent rotation of the elongate tubular member relative to the outer sheath or inner lining.

24. Steerable tube according to claim 1, further comprising an electromechanical actuator configured to controllably move the proximal bendable zone within its range of movement, and optionally to rotate the steerable tube around its longitudinal (A-A') axis.

25. Steerable tube according to claim 1, further comprising a braking mechanism, configured to prevent slidable movements by the strips relative to the outer sheath or inner lining.

* * * * *